United States Patent
Autran et al.

(10) Patent No.: US 8,182,456 B2
(45) Date of Patent: May 22, 2012

(54) DISPOSABLE ABSORBENT ARTICLES WITH COMPONENTS HAVING BOTH PLASTIC AND ELASTIC PROPERTIES

(75) Inventors: Jean-Philippe Marie Autran, Wyoming, OH (US); Donald Carroll Roe, West Chester, OH (US); Fred Naval Desai, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 420 days.

(21) Appl. No.: 11/087,368

(22) Filed: Mar. 23, 2005

(65) Prior Publication Data

US 2005/0215963 A1    Sep. 29, 2005

Related U.S. Application Data

(60) Provisional application No. 60/557,225, filed on Mar. 29, 2004.

(51) Int. Cl.
*A61F 13/15* (2006.01)
*A61F 13/20* (2006.01)

(52) U.S. Cl. .................................. 604/385.22

(58) Field of Classification Search ............. 604/385.16, 604/385.22, 385.24, 385.27
See application file for complete search history.

(56) References Cited

U.S. PATENT DOCUMENTS

| | | | |
|---|---|---|---|
| 2,413,970 A | 1/1947 | Thomas |
| 3,848,594 A | 11/1974 | Buell |
| 3,860,003 A | 1/1975 | Buell |
| 4,322,467 A | 3/1982 | Heimbach et al. |
| 4,342,314 A | 8/1982 | Radel et al. |
| 4,515,595 A | 5/1985 | Kievit et al. |
| 4,610,678 A | 9/1986 | Weisman et al. |
| 4,662,875 A | 5/1987 | Hirotsu et al. |
| 4,673,402 A | 6/1987 | Weisman et al. |
| 4,695,278 A | 9/1987 | Lawson |
| 4,699,622 A | 10/1987 | Toussant et al. |
| 4,705,584 A | 11/1987 | Lauchenauer |
| 4,834,735 A | 5/1989 | Alemany et al. |

(Continued)

FOREIGN PATENT DOCUMENTS

DE    19516037 A1    11/1996

(Continued)

OTHER PUBLICATIONS

Greg Hearn, Multistrand Elastics' Role in Diaper Performance, Nonwovens World, Apr.-May 2003, pp. 63-68.
Simulations on Crystallization in Stereoblock Poly(propylene). Idealized Structures Showing the Effects of Atactic Block Length, Macromol. Theory Simul. 7, 69-77 (1998), Huthig & Wepf Verlag, Zug.

*Primary Examiner* — Melanie Hand
(74) *Attorney, Agent, or Firm* — Charles R. Ware

(57) ABSTRACT

Absorbent articles having a liquid permeable topsheet, a liquid impermeable backsheet, and an absorbent core disposed between said topsheet and said backsheet are disclosed. The absorbent articles include a plasto-elastic material joined to or disposed on at least one of component of the absorbent article to impart sizing or shaping capabilities to the article. The plasto-elastic material has substantially plastic properties when said absorbent article is subjected to an initial strain cycle, for example, when the article is placed on a wearer, and has substantially elastic properties when subjected to a second strain cycle such as when the article is subsequently adjusted to conform to the size of the wearer. The absorbent article can be in the form of diapers, pull-on diapers, training pants, sanitary napkins, wipes, bibs, incontinence briefs or inserts.

16 Claims, 24 Drawing Sheets

U.S. PATENT DOCUMENTS

| | | | |
|---|---|---|---|
| 4,846,815 A | 7/1989 | Scripps | |
| 4,888,231 A | 12/1989 | Angstadt | |
| 4,892,536 A | 1/1990 | DesMarais et al. | |
| 4,894,060 A | 1/1990 | Nestegard | |
| 4,940,464 A | 7/1990 | Van Gompel et al. | |
| 4,946,527 A | 8/1990 | Battrell | |
| 4,963,140 A | 10/1990 | Robertson et al. | |
| 4,990,147 A | 2/1991 | Freeland | |
| 5,037,416 A | 8/1991 | Allen et al. | |
| 5,055,103 A | 10/1991 | Nomura et al. | |
| 5,057,097 A | 10/1991 | Gesp | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell | |
| 5,156,793 A | 10/1992 | Buell et al. | |
| 5,167,897 A | 12/1992 | Weber et al. | |
| 5,217,798 A | 6/1993 | Brady et al. | |
| 5,221,274 A | 6/1993 | Buell | |
| 5,236,430 A | 8/1993 | Bridges | |
| 5,242,436 A | 9/1993 | Weil et al. | |
| 5,246,433 A | 9/1993 | Hasse et al. | |
| 5,260,345 A | 11/1993 | DesMarais et al. | |
| 5,269,775 A | 12/1993 | Freeland et al. | |
| 5,302,454 A | 4/1994 | Cecchin et al. | |
| 5,330,598 A | 7/1994 | Erdman et al. | |
| 5,342,338 A | 8/1994 | Roe | |
| 5,368,584 A | 11/1994 | Clear et al. | |
| 5,387,207 A | 2/1995 | Dyer et al. | |
| 5,397,316 A | 3/1995 | LaVon et al. | |
| H1517 H | 2/1996 | Erickson et al. | |
| 5,499,978 A | 3/1996 | Buell et al. | |
| 5,507,736 A | 4/1996 | Clear et al. | |
| 5,542,942 A | 8/1996 | Kline et al. | |
| 5,547,736 A | 8/1996 | Simon et al. | |
| 5,554,143 A | 9/1996 | Roe et al. | |
| 5,554,144 A | 9/1996 | Roe et al. | |
| 5,554,145 A | 9/1996 | Roe et al. | |
| 5,556,394 A | 9/1996 | Roe et al. | |
| 5,569,232 A | 10/1996 | Buell et al. | |
| 5,569,234 A | 10/1996 | Buell et al. | |
| 5,571,096 A | 11/1996 | Dobrin et al. | |
| 5,575,783 A | 11/1996 | Clear et al. | |
| 5,580,411 A | 12/1996 | Nease et al. | |
| 5,591,152 A | 1/1997 | Buell et al. | |
| 5,594,080 A * | 1/1997 | Waymouth et al. | 526/126 |
| 5,650,222 A | 7/1997 | DesMarais et al. | |
| 5,662,758 A | 9/1997 | Hamilton et al. | |
| 5,669,897 A | 9/1997 | LaVon et al. | |
| 5,671,678 A | 9/1997 | Bolte et al. | |
| 5,749,865 A | 5/1998 | Yamamoto et al. | |
| 5,749,866 A | 5/1998 | Roe et al. | |
| H1750 H * | 9/1998 | Dobrin | 604/383 |
| 5,865,823 A | 2/1999 | Curro | |
| 5,871,607 A | 2/1999 | Hamilton et al. | |
| 5,876,391 A | 3/1999 | Roe et al. | |
| 5,897,545 A | 4/1999 | Kline et al. | |
| 5,904,673 A | 5/1999 | Roe et al. | |
| 5,910,224 A | 6/1999 | Morman | |
| 5,916,663 A | 6/1999 | Chappell et al. | |
| 5,957,908 A | 9/1999 | Kline et al. | |
| 6,004,306 A | 12/1999 | Robles et al. | |
| 6,050,985 A | 4/2000 | Lavon et al. | |
| 6,107,537 A | 8/2000 | Elder et al. | |
| 6,120,487 A | 9/2000 | Ashton | |
| 6,120,489 A | 9/2000 | Johnson et al. | |
| 6,132,409 A | 10/2000 | Vogt et al. | |
| 6,168,584 B1 | 1/2001 | Allen et al. | |
| 6,179,820 B1 * | 1/2001 | Fernfors | 604/385.27 |
| 6,193,701 B1 | 2/2001 | Van Gompel et al. | |
| 6,193,918 B1 | 2/2001 | McGuire et al. | |
| 6,245,050 B1 | 6/2001 | Odorzynski et al. | |
| 6,303,208 B1 | 10/2001 | Pelkie | |
| 6,313,372 B1 | 11/2001 | Suzuki | |
| 6,325,787 B1 | 12/2001 | Roe et al. | |
| 6,429,352 B1 | 8/2002 | Herrlein et al. | |
| 6,432,098 B1 | 8/2002 | Kline et al. | |
| 6,436,512 B1 | 8/2002 | Kauschke et al. | |
| 6,448,464 B1 | 9/2002 | Akin et al. | |
| 6,465,073 B1 | 10/2002 | Morman et al. | |
| 6,478,785 B1 | 11/2002 | Ashton et al. | |
| 6,495,229 B1 | 12/2002 | Carte et al. | |
| 6,503,236 B1 | 1/2003 | Uitenbroek et al. | |
| 6,531,025 B1 | 3/2003 | Lender et al. | |
| 6,531,027 B1 | 3/2003 | Lender et al. | |
| 6,552,245 B1 | 4/2003 | Roessler et al. | |
| 6,585,713 B1 | 7/2003 | LeMahieu et al. | |
| 6,623,468 B2 | 9/2003 | Shimoe | |
| 6,677,038 B1 | 1/2004 | Topolkaraev et al. | |
| 6,680,265 B1 | 1/2004 | Smith et al. | |
| 6,682,514 B1 | 1/2004 | Brunner | |
| 6,686,303 B1 | 2/2004 | Haynes et al. | |
| 6,703,537 B1 | 3/2004 | Roe et al. | |
| 6,827,806 B2 | 12/2004 | Uitenbroek et al. | |
| 6,833,179 B2 | 12/2004 | May et al. | |
| 6,875,710 B2 | 4/2005 | Eaton et al. | |
| 6,896,843 B2 | 5/2005 | Topolkaraev et al. | |
| 6,939,334 B2 | 9/2005 | Odorzynski et al. | |
| 6,994,761 B2 | 2/2006 | Klemp et al. | |
| 2002/0007164 A1 | 1/2002 | Boggs et al. | |
| 2002/0009940 A1 | 1/2002 | May et al. | |
| 2002/0128617 A1 | 9/2002 | Roe et al. | |
| 2002/0180097 A1 | 12/2002 | Giachetto et al. | |
| 2003/0083635 A1 | 5/2003 | Gibbs | |
| 2003/0084996 A1 | 5/2003 | Alberg et al. | |
| 2003/0087059 A1 | 5/2003 | Jackson et al. | |
| 2003/0087098 A1 | 5/2003 | Eaton et al. | |
| 2003/0088220 A1 | 5/2003 | Molander et al. | |
| 2003/0088228 A1 | 5/2003 | Desai et al. | |
| 2003/0091807 A1 | 5/2003 | Desai et al. | |
| 2003/0153894 A1 | 8/2003 | Gibbs et al. | |
| 2003/0204017 A1 | 10/2003 | Stevens et al. | |
| 2003/0233082 A1 | 12/2003 | Kline et al. | |
| 2004/0019139 A1 | 1/2004 | Hanke et al. | |
| 2004/0024109 A1 | 2/2004 | Hamersky et al. | |
| 2004/0044323 A1 | 3/2004 | Roessler et al. | |
| 2004/0049836 A1 | 3/2004 | Ashraf et al. | |
| 2004/0078018 A1 | 4/2004 | Gompel et al. | |
| 2004/0087235 A1 | 5/2004 | Morman et al. | |
| 2004/0106723 A1 | 6/2004 | Yang et al. | |
| 2004/0110442 A1 | 6/2004 | Rhim et al. | |
| 2004/0122408 A1 | 6/2004 | Potnis et al. | |
| 2004/0122409 A1 | 6/2004 | Thomas et al. | |
| 2004/0126579 A1 | 7/2004 | Creagan | |
| 2004/0127128 A1 | 7/2004 | Thomas | |
| 2004/0127131 A1 | 7/2004 | Potnis | |
| 2004/0127881 A1 | 7/2004 | Stevens et al. | |
| 2004/0134596 A1 | 7/2004 | Rosati et al. | |
| 2004/0142110 A1 | 7/2004 | Branca et al. | |
| 2005/0096623 A1 * | 5/2005 | Nhan et al. | 604/385.22 |
| 2005/0211368 A1 | 9/2005 | McGuire et al. | |
| 2005/0215963 A1 | 9/2005 | Autran et al. | |
| 2005/0215970 A1 | 9/2005 | Kline et al. | |
| 2005/0215973 A1 | 9/2005 | Roe et al. | |

FOREIGN PATENT DOCUMENTS

| | | |
|---|---|---|
| EP | 0 472 942 B1 | 9/1995 |
| EP | 0 745 433 B1 | 12/1996 |
| EP | 1 081 672 A2 | 3/2001 |
| JP | 07 089012 | 8/1995 |
| JP | 10 53963 | 2/1998 |
| WO | WO 94/01507 A1 | 1/1994 |
| WO | WO 95/16746 A1 | 6/1995 |
| WO | WO 96/24485 A1 | 8/1996 |
| WO | WO 97/47264 A1 | 12/1997 |
| WO | WO 98/46180 A1 | 10/1998 |
| WO | WO 01/27373 A1 | 4/2001 |
| WO | WO 02/060368 A2 | 8/2002 |
| WO | WO 03/039421 A | 5/2003 |
| WO | WO 03034921 A2 * | 5/2003 |
| WO | WO 03039421 A2 * | 5/2003 |

* cited by examiner

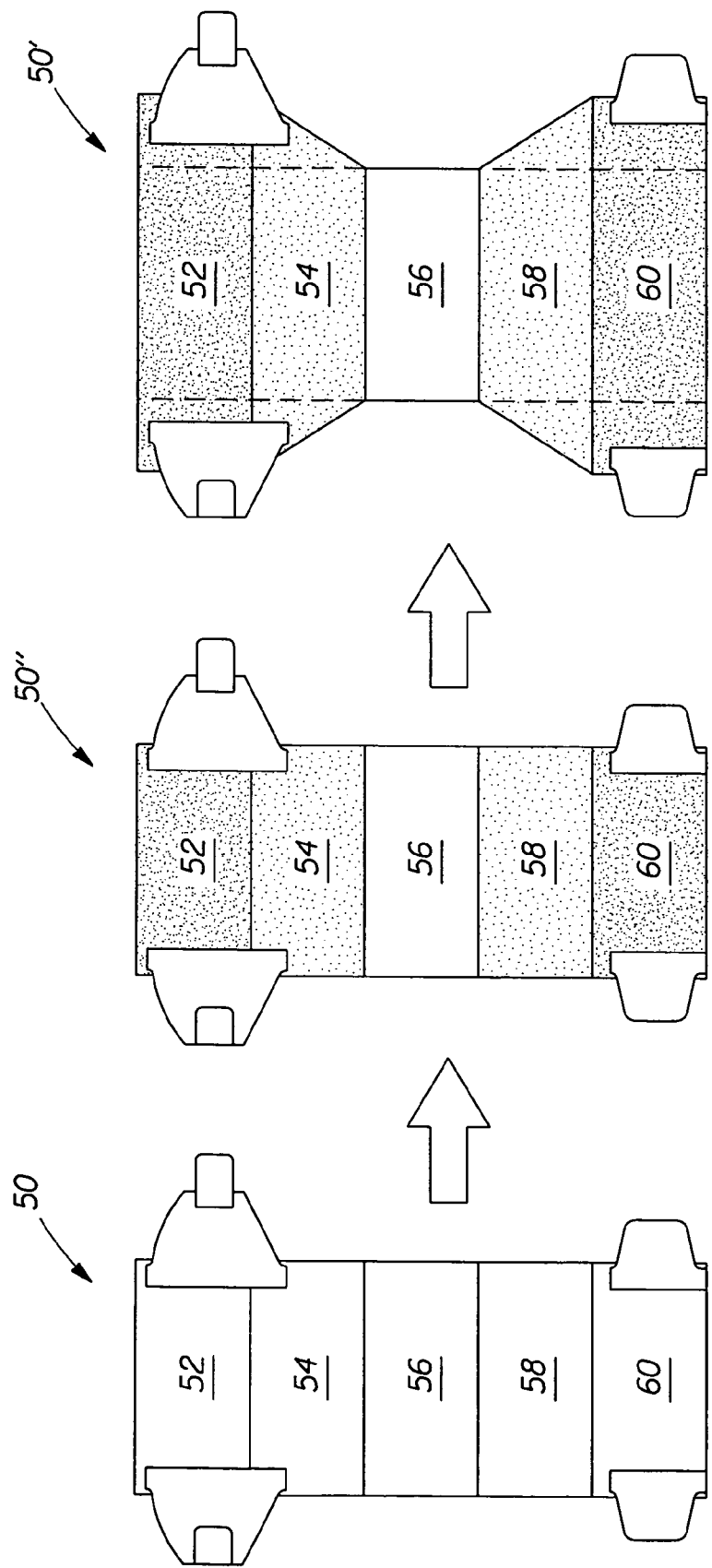

DISPOSABLE ABSORBENT ARTICLES WITH COMPONENTS HAVING BOTH PLASTIC AND ELASTIC PROPERTIES

CROSS REFERENCE TO RELATED APPLICATIONS

This application claims the benefit of U.S. Provisional Application No. 60/557,225 filed Mar. 29, 2004.

FIELD OF THE INVENTION

The present invention generally relates to disposable absorbent articles such as diapers, pull-on diapers, training pants, sanitary napkins, wipes, bibs, incontinence briefs or inserts and the like. More specifically, the invention is directed to such absorbent articles that have one or more components that have both plastic and elastic properties. Such components are used in the absorbent articles of the invention to provide the desired article shape and/or to impart the desired stress and strain properties for improved fit and comfort of the article on the wearer and/or for increased convenience of the user.

BACKGROUND OF THE INVENTION

Disposable absorbent products, such as diapers, training pants, and incontinence articles typically include stretchable materials, such as elastic strands, in the waist region and the cuff regions to provide a snug fit and a good seal of the article. Pant-type absorbent articles further include stretchable materials in the side portions for easy application and removal of the article and for sustained fit of the article. Stretchable materials have also been used in the ear portions of disposable diapers for adjustable fit of the article. However, it would be desirable to have materials that exhibit substantially plastic behavior prior to and during a shaping strain cycle, for example, when the article is initially put on a wearer, yet exhibit substantially elastic behavior after this initial shaping or donning strain cycle on the article. In this way, such desirable absorbent articles would have the ability to shape or size to the wearer to better fit conform to a wearer's body shape, yet have the ability to maintain the required tension when on a wearer to achieve sustained fit and prevent sagging and/or drooping of the article. Absorbent articles of this kind would allow the user or wearer to "permanently" adjust various areas of the absorbent article, e.g., the crotch or waist region of a diaper, either before or during the application of the article to the wearer, to adapt the article to a wearer's body shape. In the case of a diaper, better fit and comfort can also impart better functional performance such as reduced leakage since the diaper would be better fitting. Such features have heretofore not been available for absorbent articles.

There are various approaches to providing desirable stretchable properties in targeted areas of absorbent articles. Stretchable materials may be films or nonwoven fibrous webs that include elastomeric materials. Typically, such materials are stretchable in at least one, and possibly multiple, directions. However, because the films or webs are made entirely of elastomeric materials, they are relatively expensive, and they tend to have more drag on the skin surface, resulting in discomfort to the wearer of the article. Also, because the materials are elastomeric, any applied strain is substantially recovered when the force leading to the strain is removed. Sometimes, the stretchable films are laminated to one or more layers of nonwoven webs. Since typical nonwoven webs typically are made of thermoplastic fibers, they have very limited stretchability and, the resulting laminates provide considerable resistance to stretch without additional processing. It is necessary to reduce this resistance substantially in order to make functional stretch laminates. As a result, such materials have limited ability to shape, size or conform to the particularities of the wearer's anatomy upon application.

Other approaches to make stretchable materials are also known, including: stretch-bonded laminates (SBL) and necked-bonded laminates (NBL). Stretch bonded laminates are made by stretching an elastomeric material in the machine direction (MD), laminating it to one or more nonwoven substrates while it is in the stretched state, and releasing the tension in the elastomeric material so that the nonwovens gather and take on a puckered shape. Necked-bonded laminates are made by first stretching a nonwoven substrate in the machine direction such that it necks (i.e., reduces its dimension) at least in the cross machine direction (CD), then bonding the elastomeric material to the substrate while the substrate is still in the stretched, necked state. This laminate will be stretchable in the CD, at least up to the original width of the nonwoven before it was necked. Combinations of stretch bonding and neck bonding have also been known to deliver stretch in both MD and CD directions. In these approaches, at least one of the components is in a tensioned (i.e., stretched) state when the components of the laminates are joined together. Again, these materials cannot be used in absorbent articles to impart sizing or shaping features desired by users and wearers of absorbent articles.

Zero strain stretch laminates are also known. The zero strain stretch laminates are made by bonding an elastomer to a nonwoven while both are in an unstrained state. The laminates are then incrementally stretched to impart stretch properties. The incrementally stretched laminates are stretchable only to the extent afforded by the non-recovered (i.e., residual) extensibility of the laminate. For example, U.S. Pat. No. 5,156,793, issued to Buell et al., discloses a method for incrementally stretching an elastomer-nonwoven laminate web, in a non-uniform manner, to impart elasticity to the resulting laminate. These stretch laminates behave similarly to the materials described previously in that they do not have the inherent ability to be adapted to the size or shape of a wearer.

The art has also provided "elastic" materials by prestraining a substantially plastic film so as to provide films having an elastic-like behavior along at least one axis when subjected to an applied and subsequently released elongation. Such materials, known as Structural Elastic-Like Films, are described in U.S. Pat. No. 5,691,035 to Chappell.

However, in all the approaches above, the materials or laminates are made separately and then incorporated into the absorbent article. For example, the stretch laminates described herein must be cut into the appropriate size and shape, then adhesively attached to the desired location in the product in a process sometimes referred as the "cut-and-slip" process. Because of the different stretch properties required for different elements of the product, it is necessary to make a variety of laminates having different stretchability and cut the laminates to different sizes and shapes. Several cut and slip units may be needed to handle the different stretchability of the stretch laminates and to attach them to different locations of the product. As the number of cut-and-slip units and/or steps multiplies, the process quickly becomes cumbersome, complicated and expensive. These processes are suitable for modern day absorbent article manufacture and are desirable. However, it would therefore be desirable to have absorbent articles having the desired sizing and/or shaping properties, but which can be disposed in or on the absorbent article without the need for such complicated and expensive "cut-and-slip" processes.

One alternative to cut and slip processes used by the art is to print an elastomeric composition onto a substrate. Exemplary disclosures include U.S. Pat. No. 6,531,027 which discusses adhering components of an absorbent article using an adhesive printing process, PCT Application No. 03/039420 which discusses printing first and second elastomeric compositions onto a substrate where the compositions differ in at least one of the following properties: elasticity, melt viscosity, composition, shape, pattern, add-on level, and PCT Application No. WO 03/053308, which discusses printing an elastic adhesive onto an extendable substrate to provide a tensioning force during garment wear.

The polymer arts have provided materials with stretch properties that are useful in absorbent article structures. Such materials include:

Isotactic polypropylene with stereoerrors along the polymer chain as disclosed in U.S. Pat. No. 6,555,643 and EP 1 256 594 A1;

Blends of isotactic polypropylene and alpha-olefin/propylene copolymers as disclosed in U.S. Pat. Nos. 6,342, 565 and 6,500,563 and WO 03/400201; and Block-like isotactic-atactic copolymers as disclosed in U.S. Pat. Nos. 6,559,262, 6,518,378 and 6,169,151.

Based on the foregoing, it would be desirable to have absorbent articles with stretchable material having both elastic and plastic properties such that it can be sized or shaped as desired but still retains the desired degree of elasticity to facilitate sustained fit on the wearer. Although not always necessary, it would be desirable to have such a material that can be disposed easily on any specific area of the absorbent article in any desired amount. Additionally, it would be desirable to have such a material or composite having plastic and elastic properties that can be easily placed in discrete, spaced apart areas of the absorbent article via known techniques such as a "cut-and-slip" process.

SUMMARY OF THE INVENTION

The aforementioned needs in the art are met by the present invention which provides an absorbent article with a material that has both plastic and elastic properties. The absorbent article is capable of being initially stretched from its original geometry (i.e., size and/or shape) to a different geometry (i.e., larger size and/or more anatomic shape) more conducive for easy application to a wearer, and on subsequent stretching, the article is substantially elastic so as to conform to the size of the wearer for better fit. This initial stretching step may be provided during manufacture of the article, by a caregiver, or through a combination of manufacture and caregiver action. These features are especially beneficial when the absorbent article is either an open-style or pull-on diaper in which case better fit on the wearer increases comfort and leakage protection.

In accordance with one aspect of the invention, an absorbent article is provided that comprises a liquid permeable topsheet, a liquid impermeable backsheet, and an absorbent core disposed between the topsheet and the backsheet. The article may also include one or more ears or side panels, leg cuffs, fastener components, and/or a belt. The article also comprises a plasto-elastic material that may be joined to, disposed on, or even function as at least one of the topsheet, the core, or the backsheet or, alternatively one of the other components of the article, such as an ear or side panel, leg cuff, fastener, or belt. The plasto-elastic material has substantially plastic properties when the absorbent article is subjected to an initial strain cycle as the article is placed on a wearer, and having substantially elastic properties when subjected to a second strain cycle as the article is adjusted to conform to the size of the wearer and provide a tension sufficient to hold the article in the desired relative position to the wearer during use (i.e., provide sustained fit). In other aspects of the invention, the material used in the absorbent article has, according to a Hysteresis Test, at least about a 15% set upon a first application of a strain of 200%, and less than about a 15% set upon a second application of a strain of 50%. Typically, such materials also have a force at 25% elongation of between 0.005 N/cm and about 50 N/cm after the first application of a 200% strain.

In still other aspects of the invention, a package is provided that comprises at least one diaper with a plasto-elastic material as described above and a set of instructions that includes the steps of pulling a first selected portion of the diaper to increase the size of the diaper to allow for easy application to the wearer, placing the diaper on a wearer, and adjusting the size of the diaper by pulling a second selected portion of the diaper such that the diaper conforms more closely to the size of the wearer.

BRIEF DESCRIPTION OF THE DRAWINGS

FIGS. 5A, 5B and 5C illustrate another embodiment of the laminate of FIGS. 4A and 4B wherein the laminate has several gradients of plasto-elastic properties. FIG. 5A shows the laminate in its original size, FIG. 5B shows it in its intermediate stretched size, and FIG. 5C shows the laminate in its initial fully stretched or strained size;

DETAILED DESCRIPTION OF THE INVENTION

Definitions

Figure 1:
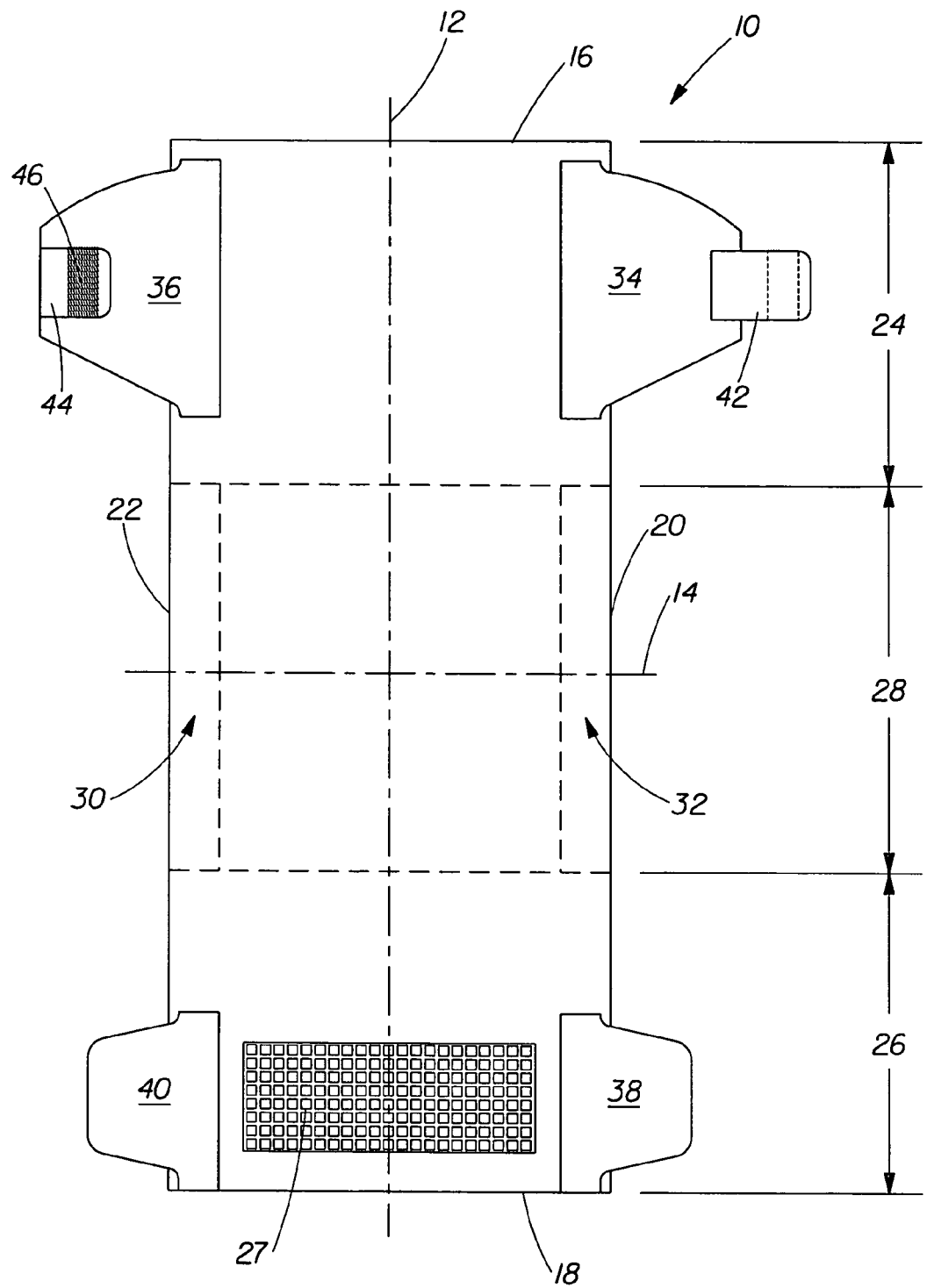
FIG. 1 is a plan view of a diaper in accordance with the invention.

As used herein, the term "polymeric blend" means a mixture of polymers which includes, but is not limited to, homopolymers, copolymers (e.g., block, graft, random and alternating copolymers), terpolymers, etc., and blends and modifications thereof which is in the form of a solid solution, that is a homogeneous mixture. Optional adjuncts may be added to the polymeric blend and, if the blend remains a solid solution, such blends are also considered polymeric blends.

As used herein, the term "polymeric mixture" means a mixture of at least two polymeric materials, in which at least a portion of one or more of the polymeric materials is immiscible in at least a portion of another of the polymeric materials, i.e., the mixture is heterogeneous.

By "stretch", it is meant that the material has the ability to extend beyond its original length in at least one dimension when subjected to a tensile force (i.e., tension) applied in the direction of that dimension. "Stretch" may be unidirectional, bi-directional, or multi-directional. The specific "stretch" properties of a material may vary along any of the stretch vectors. As used herein, stretch includes both elastic and plastic deformation.

By "elastic" or "elasticity", it is meant that a material has the ability to return to substantially its original pre-stretched dimension after an elongation-relaxation cycle such as subjecting it to tension or a force in that dimension and then releasing the elongating tension on the material (i.e., allowing the material to relax).

By "plastic", "plasticity", "extensible", or "extensibility", it is meant that a material has the ability to elongate in at least one direction under an applied tensile force without significant return when the force is removed. Substantially non-recoverable deformation is referred to as plastic deformation.

By "plasto-elastic" and "plasto-elasticity", it is meant that a material has the ability to stretch in a substantially plastic manner during an initial strain cycle (i.e., applying a tensile force to induce strain in the material, then removing the force allowing the material to relax), yet exhibit substantially elastic behavior and recovery during subsequent strain cycles. It will also be recognized that an elasto-plastic material and elasto-plasticity are equivalent descriptors of such materials.

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

"Longitudinal" is a direction running parallel to the maximum linear dimension of the article and includes directions within ±45° of the longitudinal direction. The "lateral" or "transverse" direction is orthogonal to the longitudinal direction. The "Z-direction" is orthogonal to both the longitudinal and transverse directions. The "x-y plane refers to the plane congruent with the longitudinal and transverse directions.

The term "substrate" as used herein refers to any material, including a film, an apertured film, a nonwoven web, a woven web, a foam or a combination thereof, or a dry lap material including wood pulp, cellulosic, derivatized or modified cellulosic materials, and the like, having a single layer or multiple layers. The term "fibrous substrate" as used herein refers to a material comprised of a multiplicity of fibers that could be either a natural or synthetic material or any combination thereof, including, for example, nonwoven materials, woven materials, knitted materials, and any combinations thereof.

The term "nonwoven" as used herein refers to a fabric made from continuous filaments and/or discontinuous fibers. Nonwoven fabrics include those made by carding staple fibers, airlaying or wet laying staple fibers and via extrusion processes such as spunbonding and melt blowing. The nonwoven fabric can comprise one or more nonwoven layers, wherein each layer can include continuous filaments or discontinuous fibers. Nonwovens can also comprise bi-component fibers, which can have shell/core, side-by-side, or other known fiber structures.

By "stretch zone", it is meant a portion of a region of an absorbent article having elastic, plastic, or plasto-elastic stretch properties, or a combination thereof. A stretch zone may extend throughout an entire region or feature of the article, extend across multiple regions or features, or comprise merely a portion of, one or more regions or features of the article. A region or feature may also comprise an array of individual stretch zones.

By "shaping strain cycle" is meant the steps of applying a tensile force to extend a plasto-elastic material to a desired elongation, then subsequently removing the tensile force and allowing the sample to relax, generating a substantial amount of permanent "set" or deformation in the material.

Preferred Embodiments

In a preferred embodiment, the invention provides an absorbent article having components which allow it to be stretched into a new geometry, such as a larger size and/or different shape, substantially permanently, and thereafter, is elastic in that the larger sized or reshaped article may expand and substantially contract back to this new geometry. This is particularly beneficial when the absorbent article is in the form of a diaper, pull-on diaper, training pant, sanitary napkin, wipe, bib, incontinence brief or insert in that the article can be packaged, shipped and stored in a compact size for convenience prior to use, and then when used, removed from the package and expanded to be donned conveniently on the wearer. Once on the wearer, the article may be elastically expanded and contracted for good fit and comfort. In the context of this invention, the expansion or extendibility of the article when subjected to the initial stretch or pull can be referred to as the "plastic" deformation of the article in that the article substantially retains its new geometry. It should be understood that this new geometry does not need to be retained perfectly since those skilled in the art will appreciate that a certain amount of contraction and extensibility generally exists in most plastic materials. In other words, the permanency of the initial plastic deformation of the article sometimes may not perfect. In a similar fashion, the elasticity of the article upon subsequent stretch, pull or tension after the initial force also is not perfect, but like the initial plastic deformation, generally may be elastic at the plastically deformed new geometry of the article.

Stated differently, the present invention provides an absorbent article that exhibits substantially plastic behavior prior to and during a shaping strain cycle, yet exhibits substantially elastic behavior after the initial shaping strain cycle during subsequent strain cycles. The absorbent article employs a plasto-elastic material in its plastically deformable state (i.e., prior to a shaping strain cycle) such that the wearer or caregiver may selectively elongate at least a portion of the plasto-elastic material in a straining cycle to adapt the shape of the article for convenient donning and better fit for the wearer and to establish zones of post-straining cycle elasticity. Alternatively, at least a portion of the article's plasto-elastic material may be subjected to a shaping strain cycle to create a desired article shape and establish zones of elasticity after the shaping strain during manufacture of the article. These alternate embodiments are beneficial because they allow a manufacturer to more readily provide articles with the desired geometry and stretch zones to provide superior initial and final fit of the article.

Plasto-Elastic Materials

A plasto-elastic material suitable for use in the absorbent article has, according to a Hysteresis Test described in more detail hereinafter, at least about a 15% set upon a first application of a strain of 200%, and less than about a 15% set upon a second application of a strain of 50%. Typically, plasto-elastic materials employed in the article have at least about 30% set upon relaxation from an initial 200% strain. More preferably, plasto-elastic materials exhibit more than about 40% set, more preferably more than about 50%, and most preferably, more than about 70%. Such materials typically have a set between about 30% and about 140% after a first strain cycle of 200%, more typically between about 30% and about 120% and still more typically between about 40% and about 100%.

In subsequent strain cycles, the plasto-elastic materials of the present invention that have been prestrained to 200% exhibit less than about 15% set, preferably less than about 12% set and more preferably less than about 10% set after relaxation from a second strain of 50%.

Plasto-elastic materials also may exhibit low force relaxation when held in an at least partially extended state for an extended period of time in a strained configuration after a first strain cycle. Typical plasto-elastic materials that have been prestrained to 200% exhibit less than about 70% force relaxation, preferably less than about 60%, more preferably less than 50%, and most preferably less than about 40% while held at 50% strain for 4 hours at 38° C. The force relaxation behavior is similar when held in a strained configuration at lower temperatures. Specifically, prestrained (200%) plasto-elastic materials exhibit less than about 70% force relaxation, preferably less than about 60%, more preferably less than 50%, and most preferably less than about 40% while held at 50% strain for 30 seconds at 25° C.

Suitable materials have a force at 25% elongation of between 0.005 N/cm and about 50 N/cm after the first application of a 200% strain. Preferably the materials have a force at 25% strain of between about 0.05 N/cm and about 15 N/cm more preferably between about 0.01 N/cm and about 5 N/cm. In certain embodiments the elastic resistance ranges from about 0.1N to about 3 N/cm.

In order to help insure absorbent article features that are prestrained during the manufacturing process maintain their prestrained configuration throughout the distribution system, the plasto-elastic materials of the present invention preferably maintain their prestrained dimensions when exposed to elevated temperatures for extended times. Suitably, dimensions after a first strain cycle are reduced less than about 20% after unconstrained exposure to 60° C. for two minutes. Preferably, such dimensional reduction is less than about 15%, more preferably less than about 10%. Suitable plasto-elastic stretch materials comprise multi-component polyolefin compositions that comprise a combination of at least one elastic component and at least one component which causes the composition to exhibit plastic behavior during a first strain cycle. Such compositions are described more fully in the following sections.

Elastic Component

The elastic component functions to provide the desired amount and force of recovery upon the relaxation of an elongating tension on the plasto-elastic material, especially upon strain cycles following the initial shaping strain cycle. Many elastic materials are known in the art, including synthetic or natural rubbers (e.g., crosslinked polyisoprene, polybutadiene and their saturated versions (after hydrogenation) and polyisobutylene), thermoplastic elastomers based on either multi-block copolymers such as those comprising copolymerized rubber elastomeric blocks with polystyrene blocks (e.g., styrene/isoprene/styrene or styrene/butadiene/styrene) or polyurethanes, which form a hard glassy phase which when dispersed in the elastomeric phase, anchor the polymer chains together so as to provide high mechanical integrity. Preferred elastic components include ethylene and propylene-based elastomers.

Ethylene-rich elastomers may be polymerized with various amounts of comonomers more or less randomly incorporated in the backbone in order to significantly reduce the crystallinity of the ethylene-rich backbone. Unsaturation may also be incorporated along the chain to provide reactive sites for subsequent cross-linking or vulcanization reactions via sulfur chemistry or via exposure to radiation. Crosslinking reactions link polymeric chains to one another, resulting in greater shape recoverability by minimizing chain slippage that may lead to undesirable creep or stress relaxation. Ethylene-rich elastomers functionalized with small amounts of other chemical moieties may also provide sites for subsequent strong polar interactions (as in ionomers) or for subsequent crosslinking reactions (moisture-crosslinkable silane-modified polyethylene). Ethylene-rich elastomers having a tailored composition, molecular weight and narrow composition and molecular weight distributions may also be produced using metallocene-based catalysis. In other words, the amount of residual ethylene-based crystallinity may be controlled and can function as physical crosslinks and chain-anchoring entities capable of providing increased mechanical stability and integrity to the material.

Particularly preferred elastic components include propylene-rich elastomers. In these materials, propylene represents the majority component of the polymeric backbone, and as a result, any residual crystallinity possesses the characteristics of polypropylene crystals. As in the case of ethylene-based elastomers, residual crystalline entities embedded in the propylene-based elastomeric molecular network may function as physical crosslinks, providing polymeric chain anchoring capabilities that improve the mechanical properties of the elastic network, such as high recovery, low set and low force relaxation.

An alternative means of providing anchoring capabilities is to blend inorganic particles into an amorphous polymer matrix. Suitable particles may be either microscopic (equivalent diameter >0.1 microns) or nanoscopic (equivalent diameter <0.1 microns) in size. For example, the use of miocroscopic inorganic filler materials in polyolefin plastic components of the present invention may promote the formation of micropores during tensile loading and increase the moisture vapor transmission of the material which is beneficial to the internal climate of the disposable absorbent product.

Preferred elastomeric materials comprise polypropylene polymers and include:
a) Polypropylene polymers comprising crystalline isotactic blocks and amorphous atactic blocks. In this case the crystalline blocks serve as the "anchoring" points for the amorphous blocks that lie between such anchors. Such materials are disclosed, for example in U.S. Pat. Nos. 6,559,262, 6,518,378 and 6,169,151.
b) Isotactic polypropylene with stereoerrors along the polymer chain as disclosed in U.S. Pat. No. 6,555,643 and EP 1 256 594 A1.
c) Polypropylene polymers that incorporate a low level of a co monomer, such as ethylene or a higher α-olefin into the backbone to form an elastomeric random copolymer (RCP). Exemplary materials include: VISTAMAXX as is available from ExxonMobil Chemical Co. of Houston, Tex. and OLYMPUS as is available from the Dow Chemical Company of Midland, Mich.

Plastic Component

The plastic component of the plasto-elastic compositions of the present invention functions to provide the desired amount of permanent plastic deformation imparted to the material during the initial shaping strain cycle. The higher the concentration of a given plastic component in the plasto-elastic composition, the greater the possible permanent "set" following relaxation of an initial straining force on the material. Preferred plastic components include higher crystallinity polyolefins that are themselves intrinsically plastically deformable when subjected to a tensile force in one or more directions. Exemplary polyolefins of this type include certain linear low density polyethylenes (linear low density polyethylenes), high density polyethylenes (HDPEs), polypropylene homopolymers with and random copolymers of propylene and a small fraction of another monomer such as ethylene (plastic RCPs) having a melt temperature greater than about 80° C., multi-phase systems where a rubber is dispersed in a plastic phase also known as impact copolymers (ICPs), syndiotactic polypropylene, polybutene, polyolefin waxes and their blends. Suitable polyolefin plastic components may be either miscible or immiscible with the elastic component. Preferred polyolefin plastic component materials are at least partially immiscible with the material that constitutes the elastic component so as to facilitate the interpenetrating network discussed below. For example, in embodiments wherein the elastic component of the plasto-elastic material is of the stereoisomer type described above, a RCP matrix of intermediate crystallinity (low to medium ethylene content) is a preferred plastic component (e.g., WINTEC WFX4T available from Japan Polypropylene (Tokyo, Japan)). Alternatively, if the elastic component is of the random copolymer type, then a medium or high melt temperature polypropylene homopolymer or linear low density polyethylene is a preferred plastic component (e.g., ACHIEVE from ExxonMobil Chemical Company of Houston, Tex.).

Alternate polymorphic forms of the polyolefin plastic component may also be suitable. For example, beta-crystalline forms of polypropylene may provide an easily deformable, highly ductile, tough plastic component. Upon tensile deformation, beta-crystalline polypropylene may also develop microvoids, increasing the transport properties (e.g., the ability to transport water vapor therethrough) of the plastic component, and ultimately the plasto-elastic material.

A particularly preferred plastic component is a polyolefin wax. Suitable materials of this type include microcrystalline waxes, low molecular weight polyethylene waxes and poly propylene waxes. Such waxes are advantageously used between about 5% and about 50% of the plasto-elastic composition, preferably between about 10% and about 40%. Exemplary materials include but are not limited to: a microcrystalline wax available from the Crompton Corporation of Middlebury, Conn. as Multiwax W-835; a low melting refined petroleum wax available from the Chevron Texaco Global Lubricants of San Ramon, Calif. as Refined Wax 128; a low molecular weight polyethylene as is available from Honeywell Specialty wax and Additives of Morristown, N.J. as A-C 735 and a low molecular weight polypropylene as is available from Clariant, Pigments & Additives Division of Coventry, R.I. as Licowax PP230.

Plasto-elastic Compositions

The structural and morphological characteristics of the elastic and plastic components within the plasto-elastic material, driven largely by the plasto-elastic blending process, are critical to the resultant stress-strain properties of the plasto-elastic material. Specifically, it is important to achieve microscale dispersion of any immiscible components (i.e., any discernable domains have an equivalent diameter less than about 10 microns). A suitable blending means is a twin screw extruder (e.g., the Polylab Twin Screw Extruder (available from Thermo Electron (Karlsruhe), Karlsruhe, Germany)) as are known to the art. Multicomponent polymer blend morphologies are typically dependent upon many factors such as the relative fraction and the melt rheology of each of component, their relative viscosity, as well as the compatibility of the various plastic and elastic components. For example, finer blend morphologies may be achieved between polymers having a greater thermodynamic affinity.

Suitable plasto-elastic compositions may comprise from about 95% to about 5%, by weight, of the elastic component, and preferably from about 90% to about 40%, by weight, of the elastic component. Preferably, the plasto-elastic compositions may comprise from about 5% to about 95%, and more preferably from about 10% to about 60%, by weight, of the plastic component. In some embodiments, the plasto-elastic composition may comprise more than two major components (i. e. more than two components are used at a level that is greater than about 5%).

The combination may be either in the form of a polymeric blend or a polymeric mixture, depending upon the degree of miscibility of the elastic and plastic components. If the combination forms a blend, one component can form the continuous phase that encloses dispersed particles of the other component(s). Preferably, the plasto-elastic composition comprises an interpenetrating blend having a co-continuous morphology with both phases forming interpenetrating networks.

Importantly, the polyolefin-based materials comprising the plasto-elastic composition are chosen so as to exhibit a unique combination of the plastic characteristic of traditional high-crystallinity polyolefins and the elastic characteristic of traditional elastomers. More specifically, the materials are chosen so as to provide the following mechanical performance profile to the plasto-elastic composition:

a) A low-force plastic (i.e., "permanent") deformation in response to an initial deformation strain cycle at a temperature of about room temperature and extending up to and including a temperature at, or slightly greater than, normal body temperature. Suitably, the "permanent" deformation extends is at least about 30% of the overall applied strain, preferably at least about 50%, more preferably at least about 70%. The applied strain can be either uniaxial or multivector.

b) The pre-stretched material then exhibits substantially elastic behavior upon multiple subsequent deformation cycles with low set, high recovery and low force relaxation at temperatures up to and including body temperature, especially over the range of strain applied during the original deformation cycle.

A suitable plasto-elastic material will have:

a) A relative amount of permanent dissipative viscoplastic deformation ranging from 15% to 140% of the initial strain cycle, for maximum extension values ranging from 50 to 500%, at temperatures ranging from about 20° C. to about 100° C. and initial strain rates ranging from 0.01 to 2000 $s^{-1}$. Preferably, the material can be deformed without failure at strain rates between about 1 to 2000 $s^{-1}$, more preferably 50 and 2000 $s^{-1}$, still more preferably at strain rates between 1000 and 2000 $s^{-1}$.

b) A dimensional stability of the material following the first loading cycle upon exposure to a temperature of up to 60° C. characterized by less than 20% change in the macroscopic dimensions of the material as measured by the Dimensional Stability in Storage Conditions test described in the TEST METHODS section below.

c) A permanent set value of less than 15% upon an extension of the material by a subsequent loading to a strain of at least 30% (preferably 40% and even more preferably 50%). Preferably the set is less than 10% of the strain applied upon each subsequent strain cycle;

d) A percent force relaxation less than 70%, preferably less than 50% at 50% strain (i.e., 150% elongation), for periods of up to 10 hr and for temperatures up to 40° C.

Substrate

In certain embodiments of the present invention, a substrate provides a continuous medium for deposition of the plasto-elastic material and contributes at least a portion of the ultimate strength of a stretch zone. A continuous medium is important, for example for embodiments where the embodiment comprises an array having spaced apart stretch zones. In certain embodiments (e.g., as provided by a fibrous substrate), the substrate can further provide a soft, cloth-like feel to the skin for better wearer comfort. Suitable substrate materials include but are not limited to: films, apertured films, foams, knitted fabric, woven fibrous webs or nonwoven fibrous webs as are known in the art. In some embodiments, the substrates are extensible nonwoven webs made of polyolefin fibers or filaments, such as polyethylene, or polypropylene. The substrate material may be elastic or inelastic, extensible or inextensible, stretchable or non-stretchable. Preferred substrates have a 3-dimensional morphology (i.e., via spacing between fibers, projections, holes, etc.) that facilitates the penetration of the thermoplastic elastomer into the substrate as described below.

In some embodiments the substrate cooperates with the plasto-elastic material to provide a limit to how much the plasto-elastic material may be strained during an initial strain cycle. Such limits can be advantageous, for example, when the plasto-elastic material is intended to provide a degree of size adjustability to a feature of an absorbent article where it would be undesirable for the extent strain cycle to be over large (e.g., preventing stretching a waistband so it is larger than the circumference of a wearer's waist). Such a limitation could be provided, for example, by disposing the plasto-elastic material onto the substrate while the substrate is in a shirred condition or by providing a substrate that is elastic in and of itself so that it provides a tactile signal of increasing strain to a caregiver. Suitably, a substrate of this type limits the initial strain cycle initial strain cycle such that the initial strain cycle elongates the plasto-elastic material no more than 100%. Optionally, the substrate limits the initial strain cycle such that the initial strain cycle elongates the plasto-elastic material no more than 75%.

Structures Comprising a Substrate and a Plasto-elastic Material

The plasto-elastic materials can be placed onto a substrate in defined areas of the absorbent article or a component thereof via known deposition techniques such as printing (including gravure, offset, letterpress and screen techniques), extrusion coating, roll coating and the like. For embodiments where the substrate has been shirred, it may be particularly preferable to dispose the plasto-elastic material onto the shirred substrate using an extrusion process that forms the plasto-elastic material into a substantially continuous form (e.g., extrusion coating or extrusion of strands of the material). When formed in this manner the plasto-elastic material can advantageously be disposed between two layers of the substrate to form a stretch laminate.

Applications of Plasto-elastic Materials to Absorbent Articles

Figure 2:
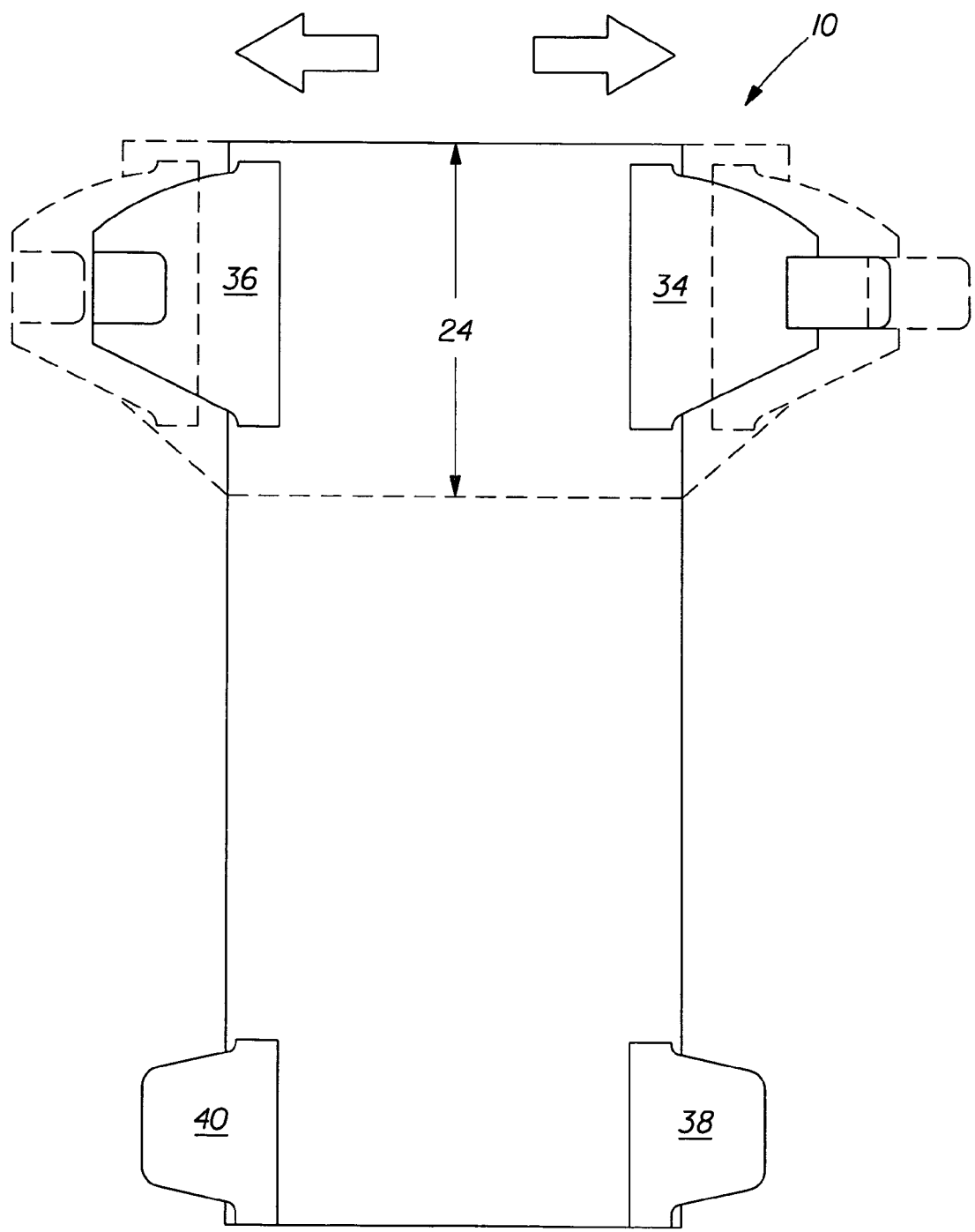
FIG. 2 is another plan view of the diaper of FIG. 1 in accordance with the invention in which the diaper is shown in dashed lines after the initial stretching, straining or pulling of the diaper ears by the user.
Figure 3:
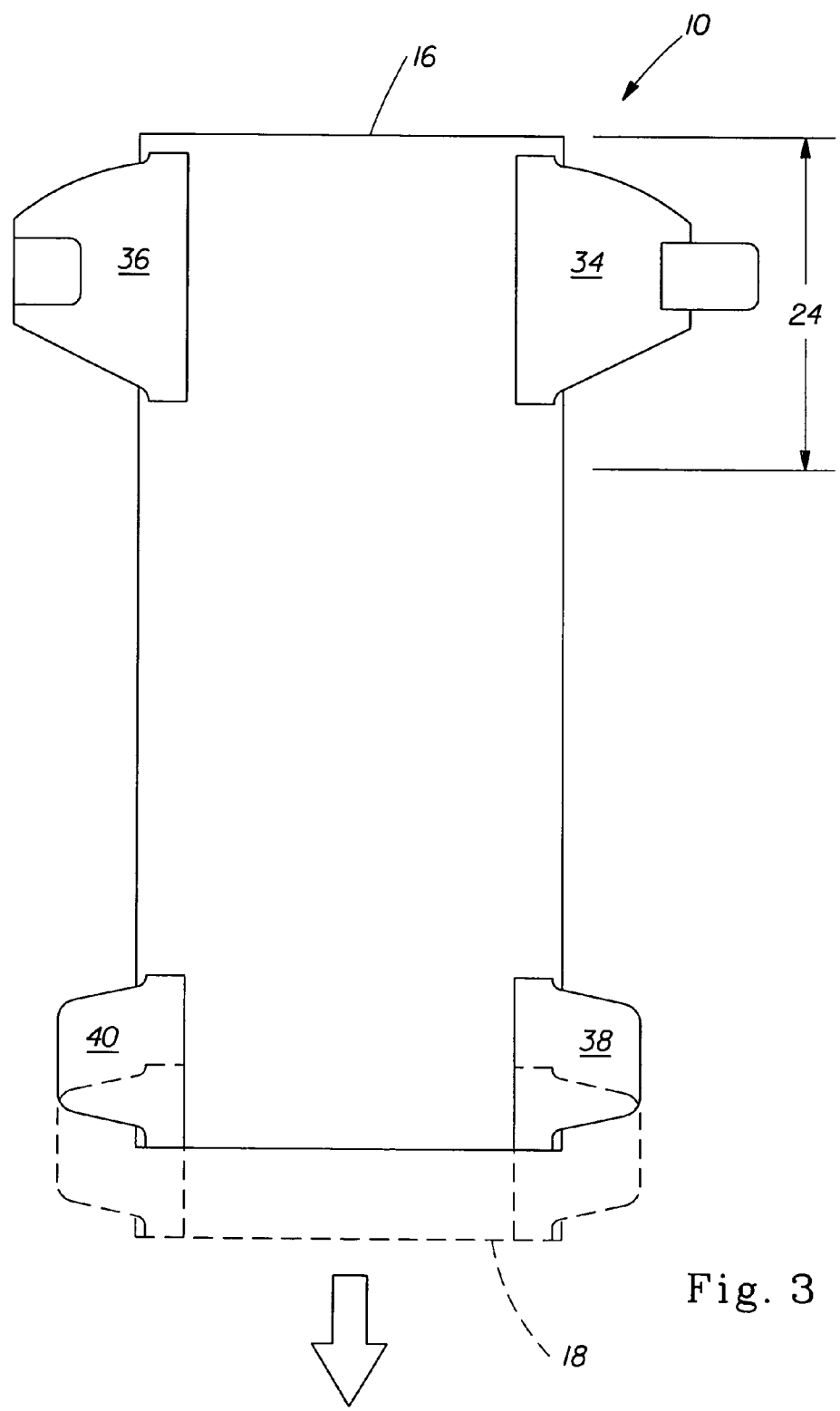
FIG. 3 is another plan view of the diaper of FIG. 1 in which the front end portion of the diaper is initially pulled, stretched or strained by the user before donning on the wearer wherein the pulled or stretch diaper is shown in dashed lines.

Referring collectively to FIGS. 1-3, an absorbent article in the form of an open-style or taped diaper 10 is depicted. It should be understood that while FIGS. 1-3 depict a diaper, the present invention also contemplates other wearable absorbent articles that encircle or enclose at least a portion of a wearer's anatomy or which are otherwise secured to a wearer. The diaper 10 has a longitudinal centerline 12 and a lateral centerline 14 as a frame of reference for this discussion. The diaper 10 may have a pair of opposed longitudinal edges 16 and 18, a pair of opposed lateral edges 20 and 22, a rear waist region 24, a front waist region 26, a crotch region 28 disposed intermediate the front and rear waist regions 26 and 24, respectively, and a pair of leg regions 30 and 32. The exact size of these various regions vary according to the size of the diaper 10, but generally speaking, the crotch region 28, front waist region 26 and rear waist region 24 represent equal one-third portions along the longitudinal centerline 12. The leg regions 30 and 32 generally represent the one-quarter areas across the width of the diaper 10 in the crotch region 28, and the crotch region 28 itself, represents the remaining center two-quarters or one-half the width of diaper 10.

The diaper 10 also may comprise one or more ear or side panels 34, 36, 38 and 40 disposed laterally outboard of the front waist region 26 and/or rear waist region 24. In closable diaper 10 embodiments, at least one fastener element 42 is disposed on one or more of side panels 34 and 36 and is adapted to be secured to at least a portion of the longitudinally opposing front side panels 38 and 40, or a portion of the outer surface of the front waist region 26 or a component thereof. An accompanying fastener element 44 is shown in a folded back configuration to expose the mechanical fasteners 46, which shown as hooks for a hook-and-loop fastening systems commercially available from 3M or Velcro Industries. The fastener element 44 may be capable of engaging loop material embodied in a landing zone 27 located on the outer surface of the diaper 10.

Any one or more of regions 24, 26, 28, 30, 32, 34, 36, 38, 40, 42 or 44 may comprise a stretch zone or array of stretch zones comprising the plasto-elastic material to provide the desired plastic deformation upon the initial stretch (i.e., upon a shaping strain cycle), and thereafter on subsequent strain cycles, have the desired elasticity in accordance with the present invention. In this way, the diaper 10 may preferably be configured to adapt to the specific wearer's anatomy upon application and to maintain coordination with the wearer's anatomy during wear (i.e., the fit should remain the same with minimal sagging, achieving sustained fit.). Any region of the diaper 10 may include a stretch zone that may comprise at least one stretch material, composite, treatment, element, or area. The front waist region 26 and/or the rear waist region 24 and/or side panel regions 34, 36, 38 and/or 40 preferably include at least one stretch zone of plasto-elastic material in order to accommodate a wider range of wearer waist dimensions (i.e., provide a wider fit range) and/or to provide sufficient tension around the waist circumference of the wearer. This provides sufficient normal force to the wearer's skin so as to anchor the diaper 10 with respect to the wearer's anatomy, thereby providing sustained fit.

As can be seen in FIGS. 2 and 3, the diaper 10 is depicted in solid lines upon removal of diaper 10 from its package. In dashed lines, the diaper 10 is depicted after being subjected to a shaping strain cycle. Subsequent strain cycles along the same strain vectors extend the product dimensions along those vectors beyond the dashed lines, but upon relaxation of the applied tension, the article elastically contracts back to the size/geometry shown in dashed lines. In FIG. 2, the stretch zone may be located in one or more of the rear waist region 24 and/or side panels 34 and/or 36. In FIG. 3, the stretch zone may be in one or more of the crotch region 28, and/or, front waist region 26, and/or side panels 38 and 40. As seen in FIG. 3, the diaper 10 may be extensible longitudinally.

Each stretch zone or array of stretch zones may have continuous or discontinuous properties in any direction wherein the varying properties include chemical composition, elasticity, extensibility, maximum elongation, stress/strain properties, vectors or angles, basis weight, geometry, dimensions, 3-dimensional morphology, visual distinctiveness, and the like. A stretch zone having continuous properties generally comprises a single constituent (i.e., material, treatment, composite, etc.) having relatively homogeneous properties. Alternatively, arrays having discontinuous properties may comprise a single stretch zones with non-homogeneous properties or a pattern of at least two stretch zones having the same or different properties. Suitable stretch zone patterns include straight or curved lines or bands, rectilinear shapes, curvilinear shapes, other regular or irregular geometric shapes, and combinations thereof which will be described in more detail hereinafter. Two stretch zones or stretch zone patterns may be longitudinally separated or adjacent, laterally separated or adjacent, or the stretch zones or stretch zone patterns may be at least partially overlapping. Within a pattern, the individual stretch zones may vary in property, geometry, relative orientation, spacing, or elasticity or extensibility. In certain embodiments, at least a portion of at least one stretch zone may be visually distinct. Stretch zones may be combined with other elastic, extensible, or inextensible materials, such as films, webs, strands, and the like to form laminates.

Figure 4B:
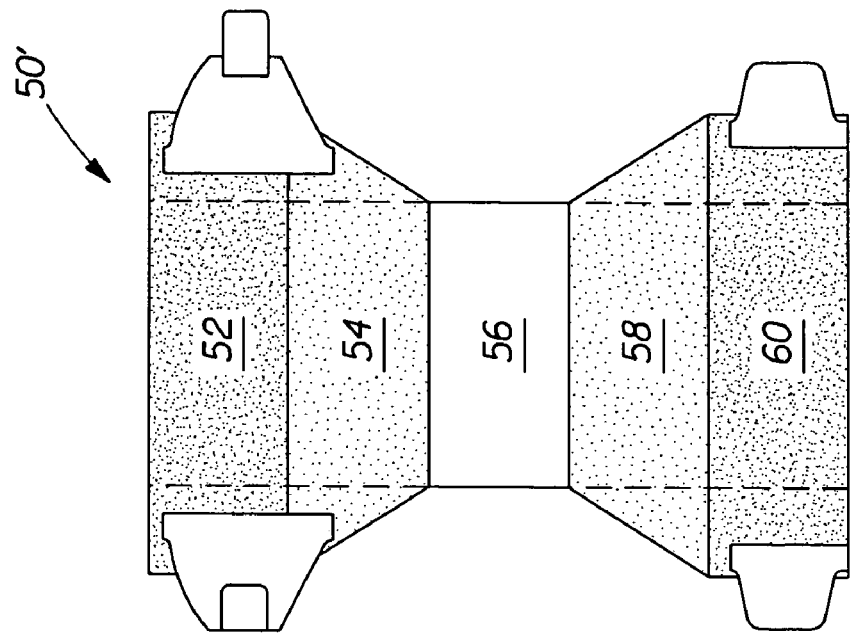
FIGS. 4A and 4B illustrate a laminate in its pre-strained original size and in its post-initial strained state in accordance with the invention.
Figure 4A:
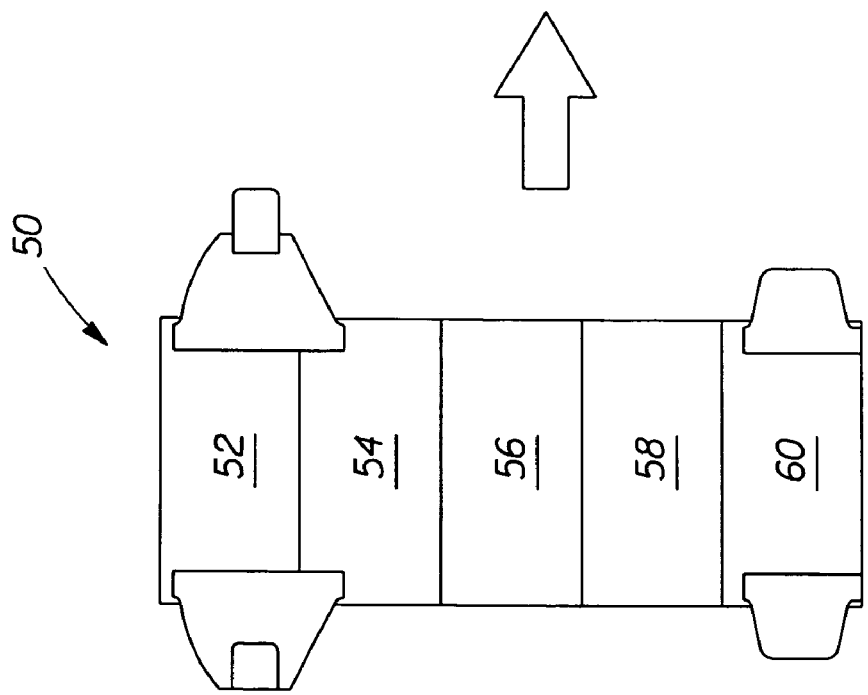

An exemplary diaper chassis comprising arrays of stretch zones is diaper chassis 50 of the diaper 10 is shown in FIGS. 4A and 4B. The diaper chassis 50 may include a liquid impermeable backsheet and an outer cover made of a nonwoven material. Other chassis components may be included but are not depicted for purposes of clearly showing the multi-variant arrays of the present invention. The backsheet may be made of the plasto-elastic material or the plasto-elastic material may be disposed on a standard liquid impermeable backsheet material in a way which creates different arrays of stretch zones in regions 52, 54, 56, 58 and 60 as described previously. By way of example, region 52 may be activated or pre-strained very heavily, while regions 54, 56, 58 and/or 60 are subjected to little to no (i.e., zero) activation or pre-straining during manufacture. In certain cases for purposes of enhancing fit on a wearer, the various stretch zone properties are symmetrical in that regions 52 and 60 have similar properties, regions 54 and 58 also have similar properties while region 56 has a third type of plasto-elastic property. It should be understood, however, that this is not necessary and the individual regions 52, 54, 56, 58 and 60 may vary individually and widely in terms of plasto-elastic properties, size, shape, and composition without deviating from the scope of the invention. The diaper chassis 50' is shown in a typical shape more closely sized and shaped to the wearer's needs after the initial shaping strain cycle performed during manufacture of the article and may be ready for donning on the wearer immediately after the diaper is removed from its package.

In a similar fashion as FIGS. 4A-B, FIGS. 5A-C depicted the diaper chassis 50 with regions 52, 54, 56, 58 and 60 as described previously, but includes an alternative embodiment in which regions 52, 54, 56, 58 and 60 are partially pre-stretched or strained during manufacture. This provides the user with an intermediate diaper chassis 50" as depicted in FIG. 5B which may be more closely sized and shaped to the wearer's needs by the wearer of caregiver prior to the donning of the article. The intermediate diaper chassis 50" may be accomplished via standard activation or stretching manufacturing techniques which are described in U.S. Pat. No. 5,518,801 and other patents referenced hereinafter. In these embodiments, the intermittent activation techniques described in the above-referenced patent may perform a shaping strain cycle on portions of the region, leaving other portions, such as narrow bands, unstrained and able to cause the overall region geometry to be held in its original state. Due to the pre-straining of a large portion of the plasto-elastic material in the formation of the intermediate chassis, the wearer or caregiver may perform the final shaping strain cycle (i.e., of the previously unstrained portions or bands) using relatively lower forces, increasing the ease of use for the wearer or caregiver prior to or during the donning of the article.

In alternate embodiments, all or part of the stretch zone area (i.e., the portion of a region having a plasto-elastic material disposed thereon) may be subjected to only a portion of the shaping strain cycle (i.e., the strain induced may be below a critical threshold value) by the manufacturer. The wearer or caregiver would subsequently need to induce less strain into the stretch zone in order to achieve the final article geometry prior to or during the donning of the article, improving the convenience and ease-of-use of the article.

Reference is now made to FIGS. 6, 7 and 8A-B which show a which show a pant 70. The term "pant", as used herein, refers to disposable garments having a waist opening and leg openings designed for infant or adult wearers. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433, 5,569,234, 6,120,487, 6,120,489, 4,940,464, 5,092,861, U.S. patent application Ser. No. 10/171,249, entitled "Highly Flexible And Low Deformation Fastening Device", filed on Jun. 13, 2002; U.S. Pat. Nos. 5,897,545, 5,957,908.

Pant 70 may include stretch zones or arrays of stretch zones to impart the desired plastic and elastic properties so that it can be donned on the wearer easily and sustain better fit and comfort. For example, a caregiver may provide a first strain cycle to enlarge waist opening 75 so as to be larger than a wearer's hip circumference so as to ease donning pant 70. Waist opening 75 could then relax back to a circumference defined by the set of the materials comprising elements of pant 70 adjacent the waist opening thereof. Exemplary features include, but are not limited to ears, side panels and belts as are discussed herein. Such features may also be partially prestrained during the manufacturing operation so as to ease the task of the caregiver in the first straining cycle.

Figure 6:
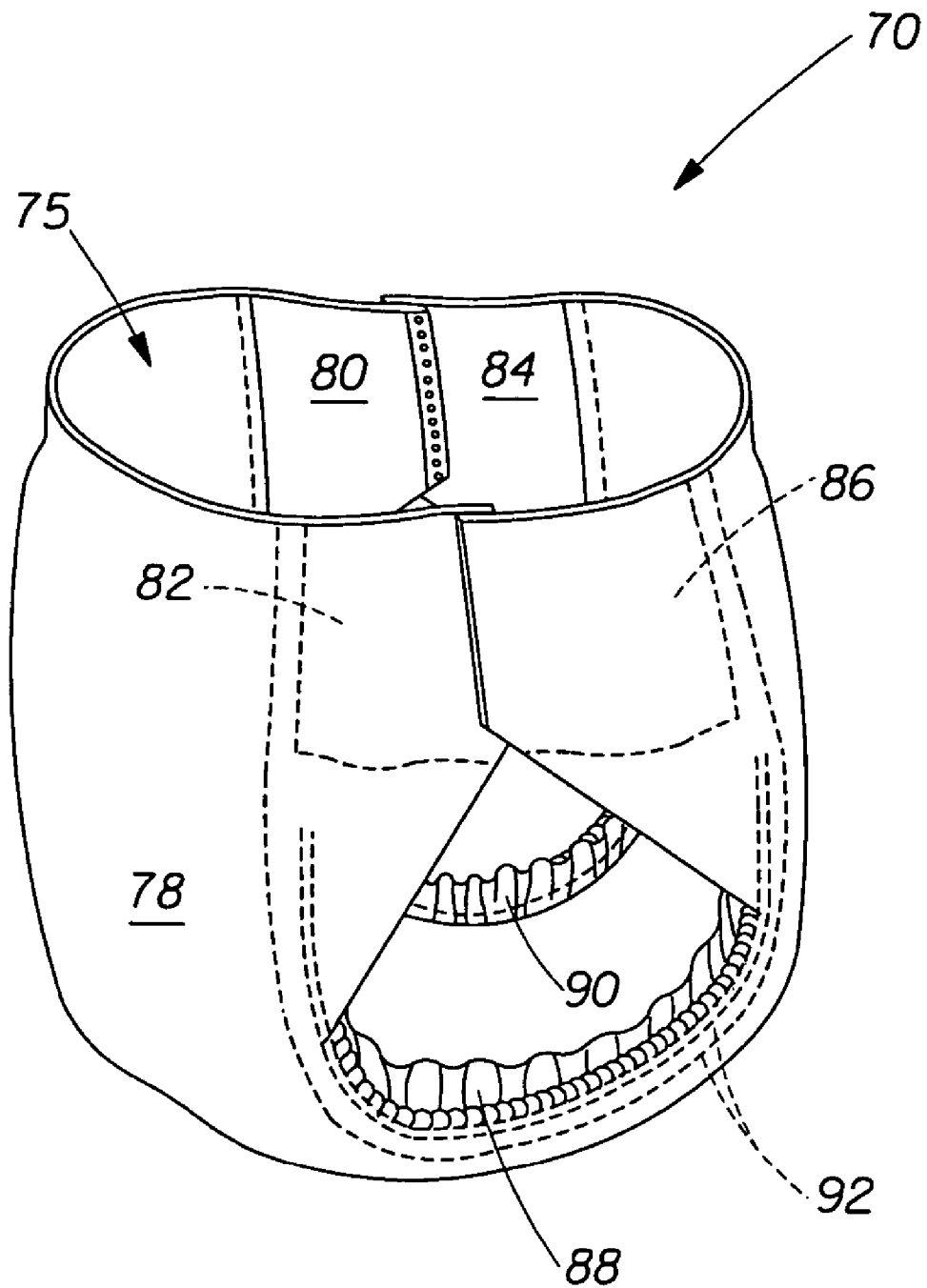
FIG. 6 is a perspective view of a pull-on diaper in accordance with the invention.
Figure 7:
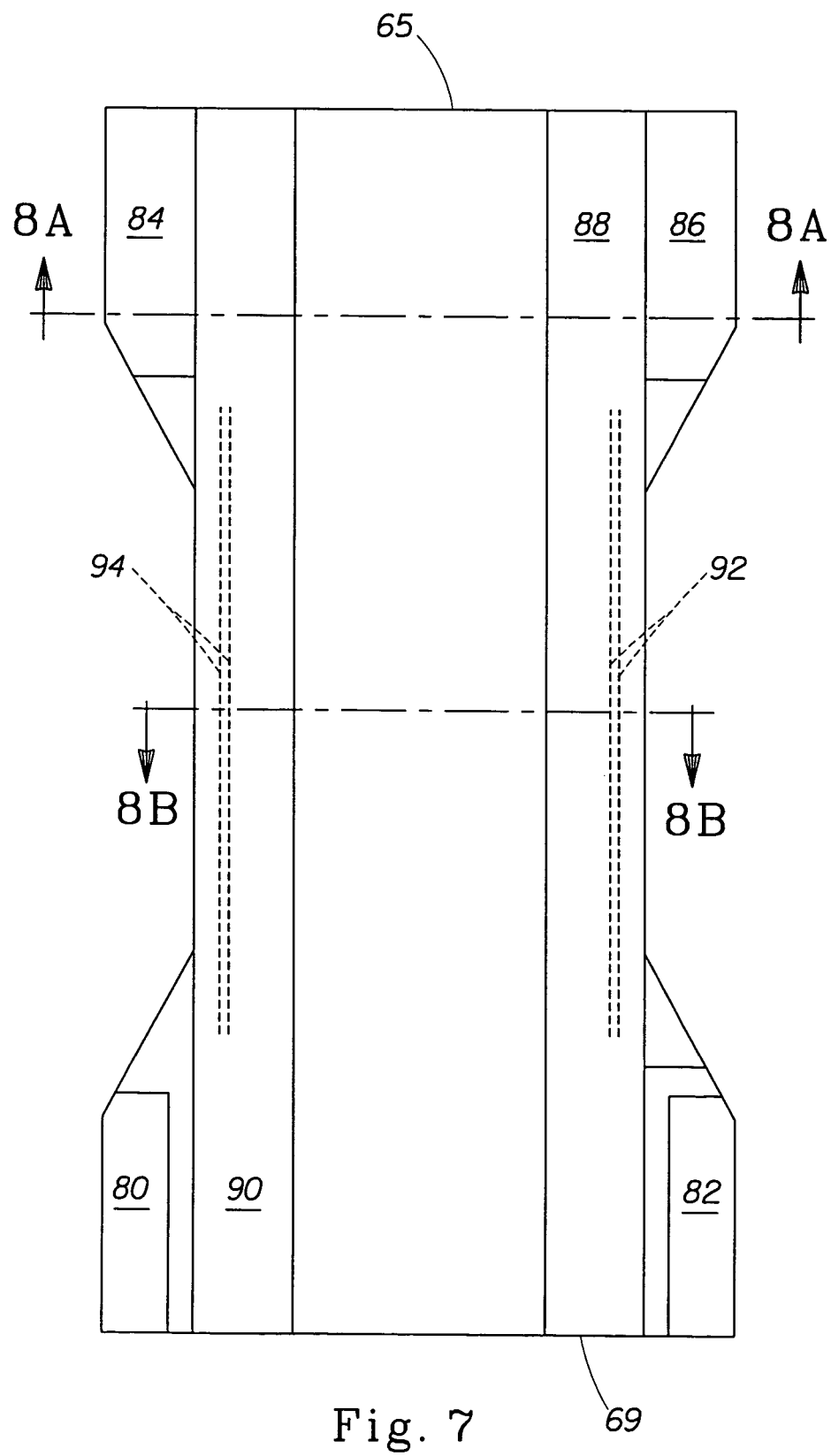
FIG. 7 is a plan view of the pull-on diaper of FIG. 6.
Figure 8A:
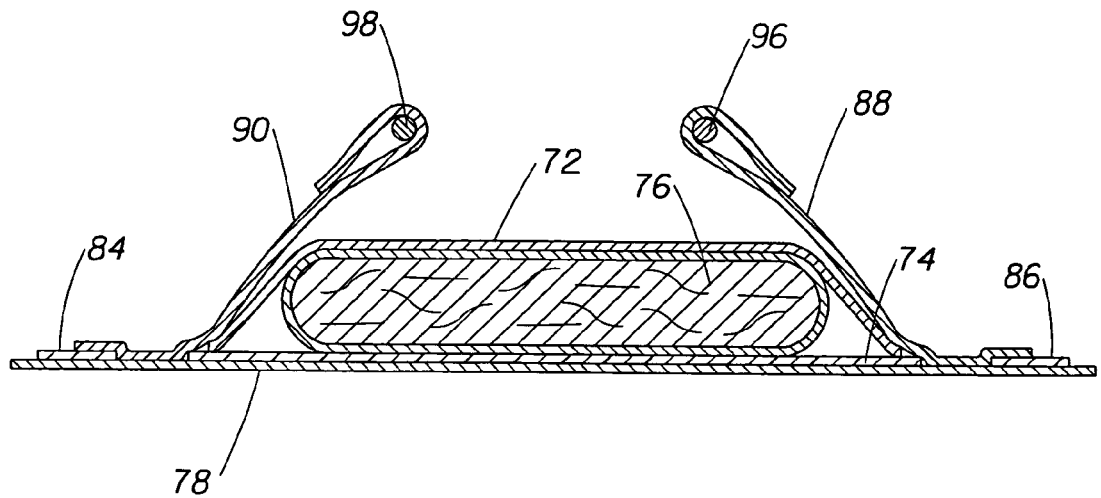
FIGS. 8A and 8B are cross-sectional views of the pull-on diaper shown in FIGS. 6-7.
Figure 8B:
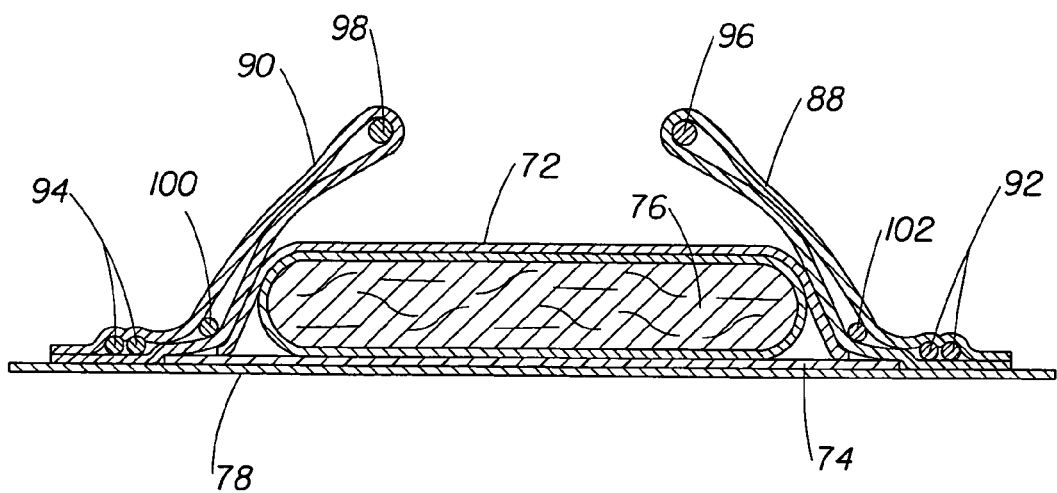

For pant 70, similar to the diaper 10, stretch zones may be included anywhere on the pant diaper 70. FIG. 6 is a perspective view of pant diaper 70 and FIG. 7 shows pant diaper 70 in a plan view. As can be seen most clearly in FIGS. 8A-B, the pant diaper 70 may include an absorbent assembly including liquid permeable topsheet 72, a liquid impermeable backsheet 74, and an absorbent core 76 disposed between the topsheet 72 and the backsheet 74. On the outer surface of the pant diaper 70, an outer cover 78 typically comprising a nonwoven is disposed. Two pair of side panels 80, 82 and 84, 86 are attached to the outer cover 78, which in turn, is attached to the backsheet 74 of the absorbent assembly so as to form a pair of leg openings and a waist opening for the wearer. Preferably, stretch zones areas are included with a stretchable material, preferably a plasto-elastic material, joined to or disposed on at least one of the side panels 80, 82, 84 and/or 86 to provide a stretch zone or array therein. The stretch zones or arrays thereof may also be incorporated into pant 70 in a waist feature (not shown but similar to those shown in FIGS. 11A-D) that is disposed adjacent end edges 65 and 69, barrier leg cuffs 88 and 90. A plasto-elastic material may also be used to form the leg elastics 92, 94, and/or in the barrier leg cuff elastics 96, 98, 100 and 102.

Belt structures (not shown) may also comprise the stretch zones of the present invention. One such alternative structure comprises the ear and/or side panel and at least a portion of the waist functionality. In another alternative belt structure, a belt completely encircling a wearer's waist (i.e., a 360 degree belt) may be formed, referring to FIG. 7 for example, by depositing one or more laterally oriented stretch zones (or an array thereof) adjacent the front and rear waist edges 65, 69 so as to form a band of tension about the wearer's waist.

Reference is made to FIGS. 9A-I in which various side panels 104, 105, 10, 10, 111, 113, 115, 117 and 119 are depicted for a closable open or taped diaper 112. It should be understood that the side panels 105, 10, 10, 111, 113, 115, 117 and 119 as described herein are interchangeable with any of the side panels or ears described in FIGS. 1-8 of the diaper 10 or pant diaper 70. The stretch zone arrows 116 are depicted to show the various force vectors that may be desirable in a typical side panel. The size of a given stretch zone or array of stretch zones in a region of the diaper 112 is dependent on the function of the stretch zone and the desired tension/extension vectors in that given region of the diaper 112. Each stretch zone may be smaller or larger than the region of the diaper 112 in which it is primarily disposed. A given stretch zone may overlap other regions of the diaper 112.

Figure 9A:
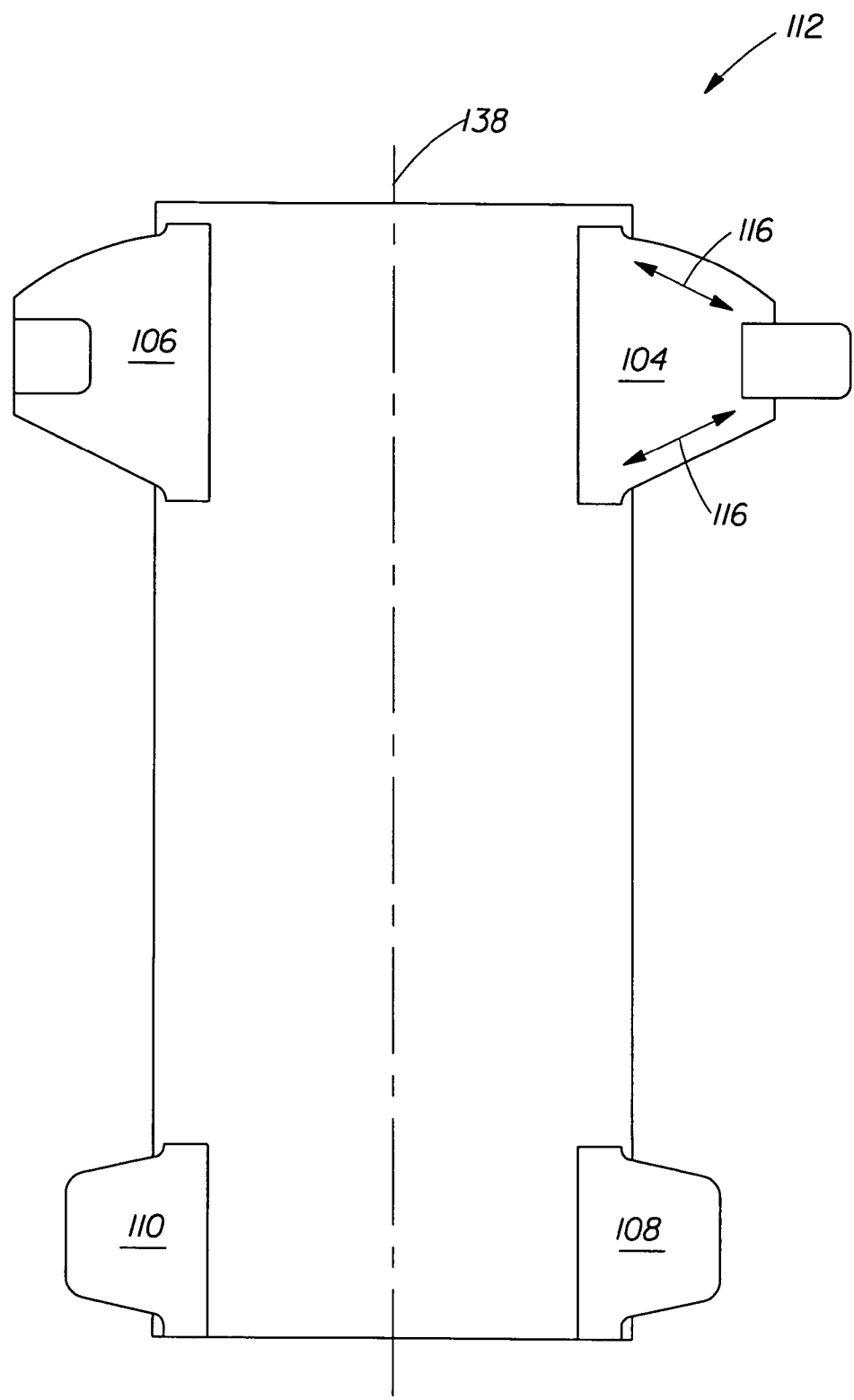
FIGS. 9A-I show the diaper of FIG. 1 in which the diaper ears have plasto-elastic material in various designs.
Figure 9B:
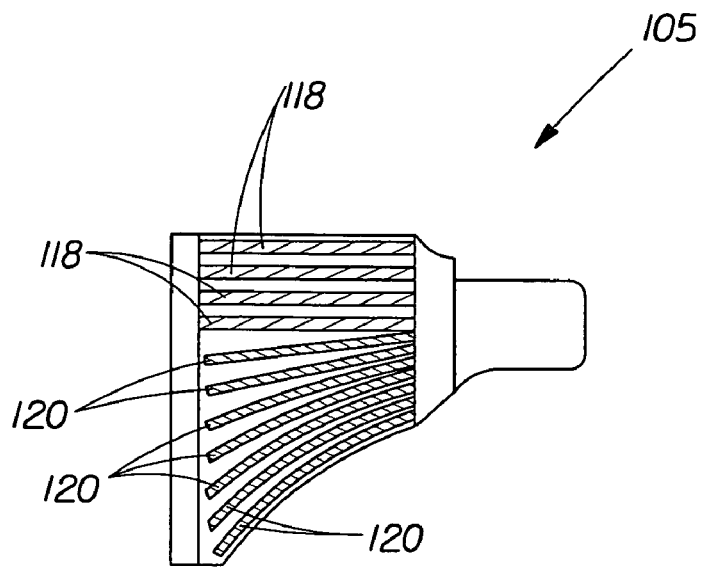
Figure 9C:
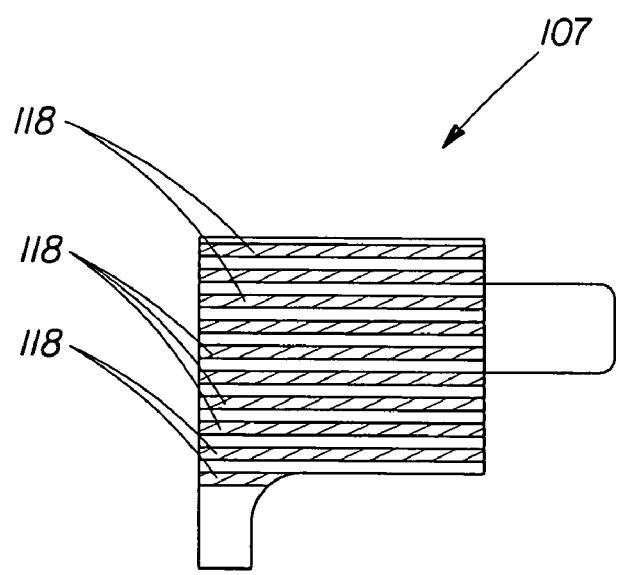
Figure 9D:
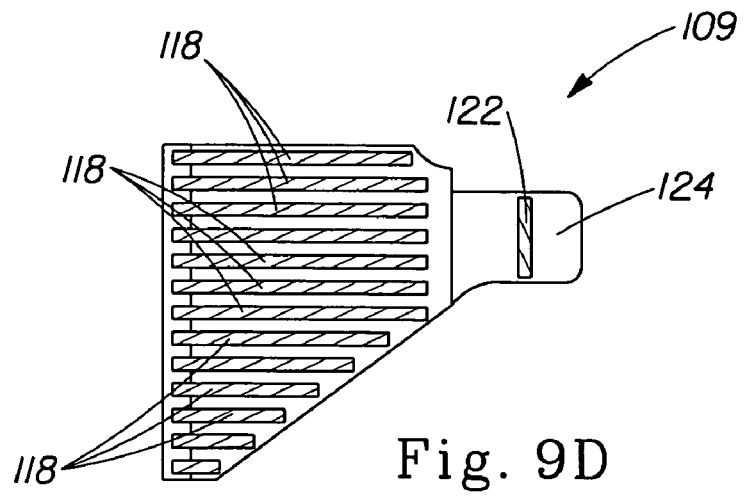
Figure 9E:
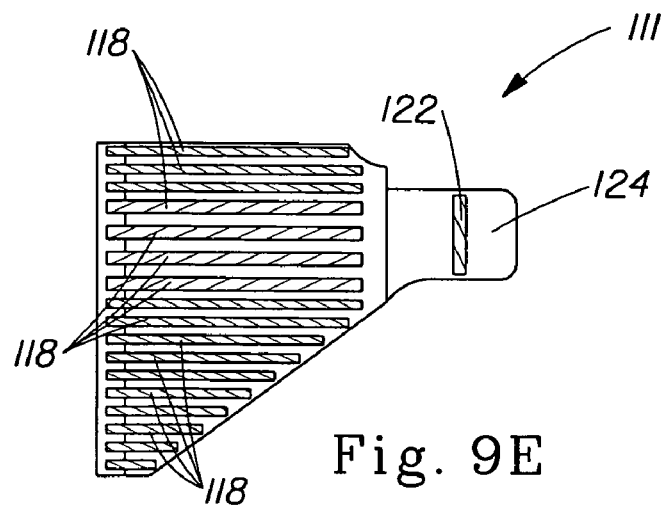
Figure 9F:
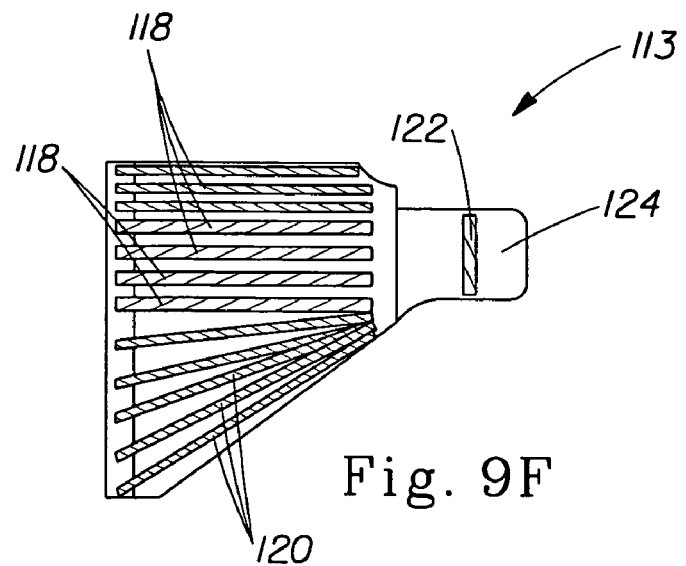

Referring to FIGS. 9B-H, various linear stretch zones 118 of plasto-elastic material in side panel 105 may be configured as lines or strands generally having widths less than about 2 mm and typically less than about 1 mm. Linear stretch zones 118 may be configured as bands generally have widths between about 2 mm and about 20 mm and aspect ratios ranging from about 2:1 to about 100:1. Linear stretch zones 118 may also be disposed at an angle with respect to the lateral centerline 151 (FIGS. 9B and 9F). Preferred angles are in the range 0±70°. Stretch zones having a predominately lateral orientation are generally wider and have a higher modulus than those having a generally longitudinal orientation. Curved stretch zones 120 may be either concave or convex with respect to the longitudinal or lateral centerlines 150, 151, or both and may have radii of curvature greater than about 1 mm, preferably greater than about 10 mm, more preferably greater than about 50 mm. The curvature may optionally be variable over the length or "path" of the stretch zone 120. Alternatively, curved stretch zones 120 may comprise a spiral or an overlapping or entangled configuration (not shown). Typically, the thickness of stretch zones 118 and/or 120 may be in the range of about 0.02 mm to about 5 mm and the basis weight is in the range of about 20 g/m$^2$ to about 300 g/m$^2$.

Suitable stretch zone 118 or 120 shapes (not all shown) include rectangles, circles, ellipses, diamonds, triangles, parallelograms, trapezoids, wedges or other sections of circles or ellipses, other polygons, or other irregular enclosed shapes.

Figure 9G:
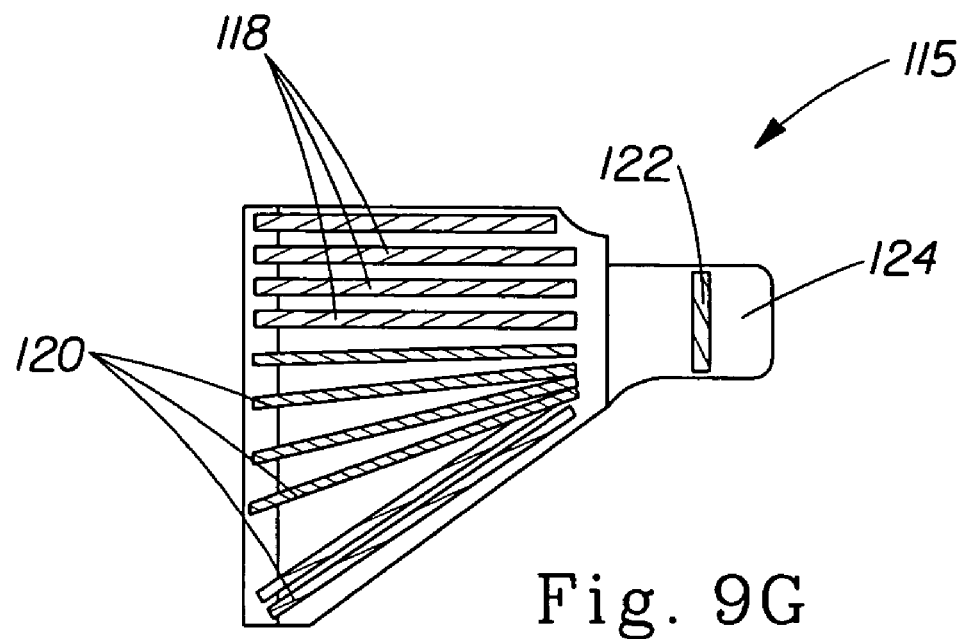
Figure 9H:
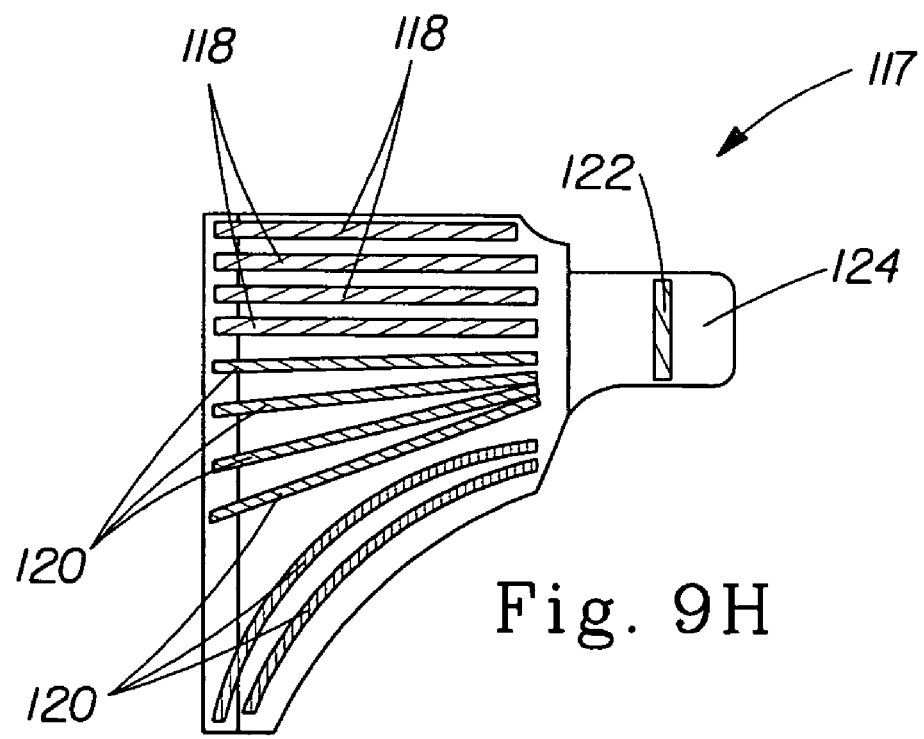

Additional exemplary embodiments of the invention are shown in FIG. 9C with side panel 107, FIG. 9D with side panel 109, FIG. 9E with side panel 111, FIG. 9F with side panel 113, FIG. 9G with side panel 115, and FIG. 9H with side panel 117. All of the side panels 109, 111, 113, 115, 117 may be integral with or separately attached to the diaper chassis of the diaper 10 or pant diaper 70 described previously. Similarly, all of the linear stretch zones 118 and 120 may be made with a plasto-elastic material as described herein. FIGS. 9D-9H show additional stretch zones 122 applied to or formed as part of the fastener element 124 to impart the desired plastic and elastic properties of the present invention. This may be particularly useful when the user is adjusting the fit of the diaper 10 or diaper pant 70 after it is on the wearer.

Alternatively, an array of linear stretch zones 118 or curved stretch zones 120 or both may comprise a spiral or an overlapping or entangled configuration, for example a cross hatch array. Suitable stretch zone shapes (not shown) include rectangles, circles, ellipses, diamonds, triangles, parallelograms, trapezoids, wedges or other sections of circles or ellipses, other polygons, or other irregular enclosed shapes.

Figure 9I:
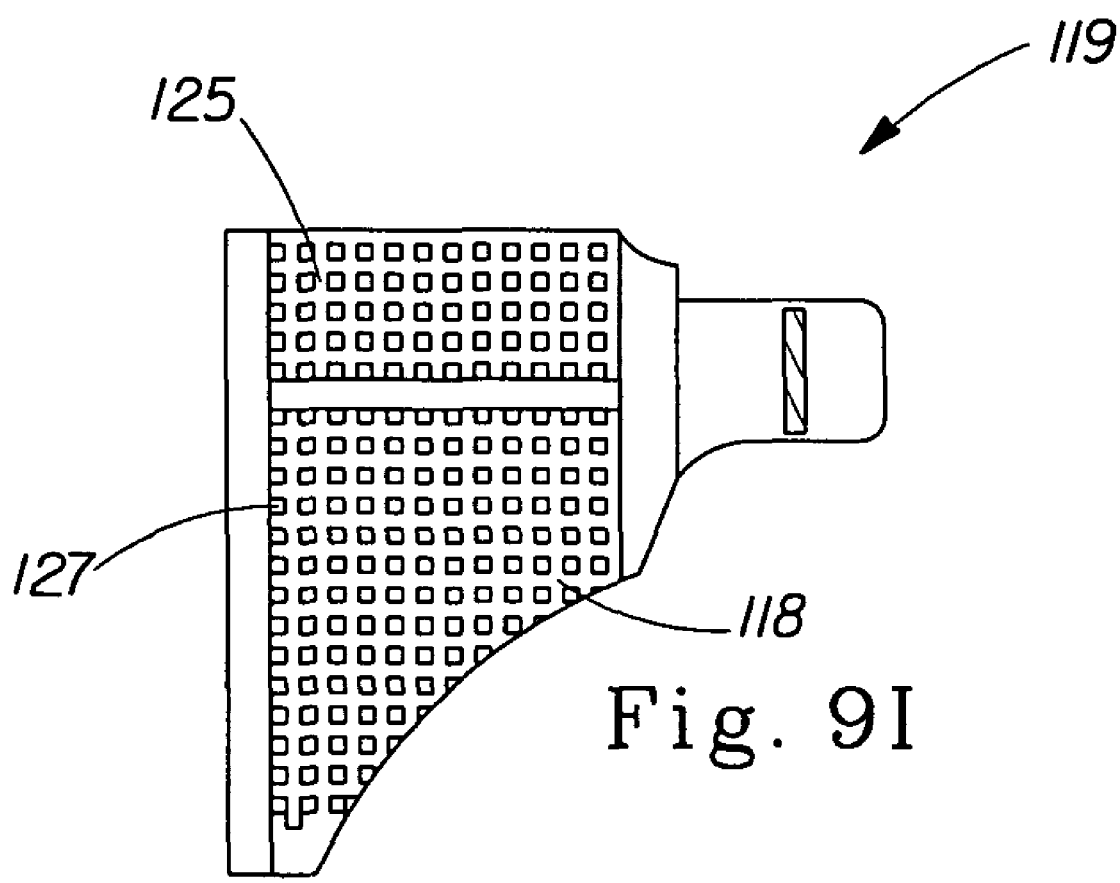

One particularly preferred embodiment of an array of stretch zones is shown in FIG. 9I where side panel 119 comprises a pair of cross hatch arrays 125, 127. As shown therein, both of arrays 125, 127 comprise a plurality of linear stretch zones 118 in an overlapping, cross hatch pattern where the individual stretch zones 118 have either a predominately lateral orientation or a predominately longitudinal orientation. As will be recognized and described herein, the stretch zones 118 can also be at an angle other than 0° or 90° with respect to the centerlines.

Figure 10A:
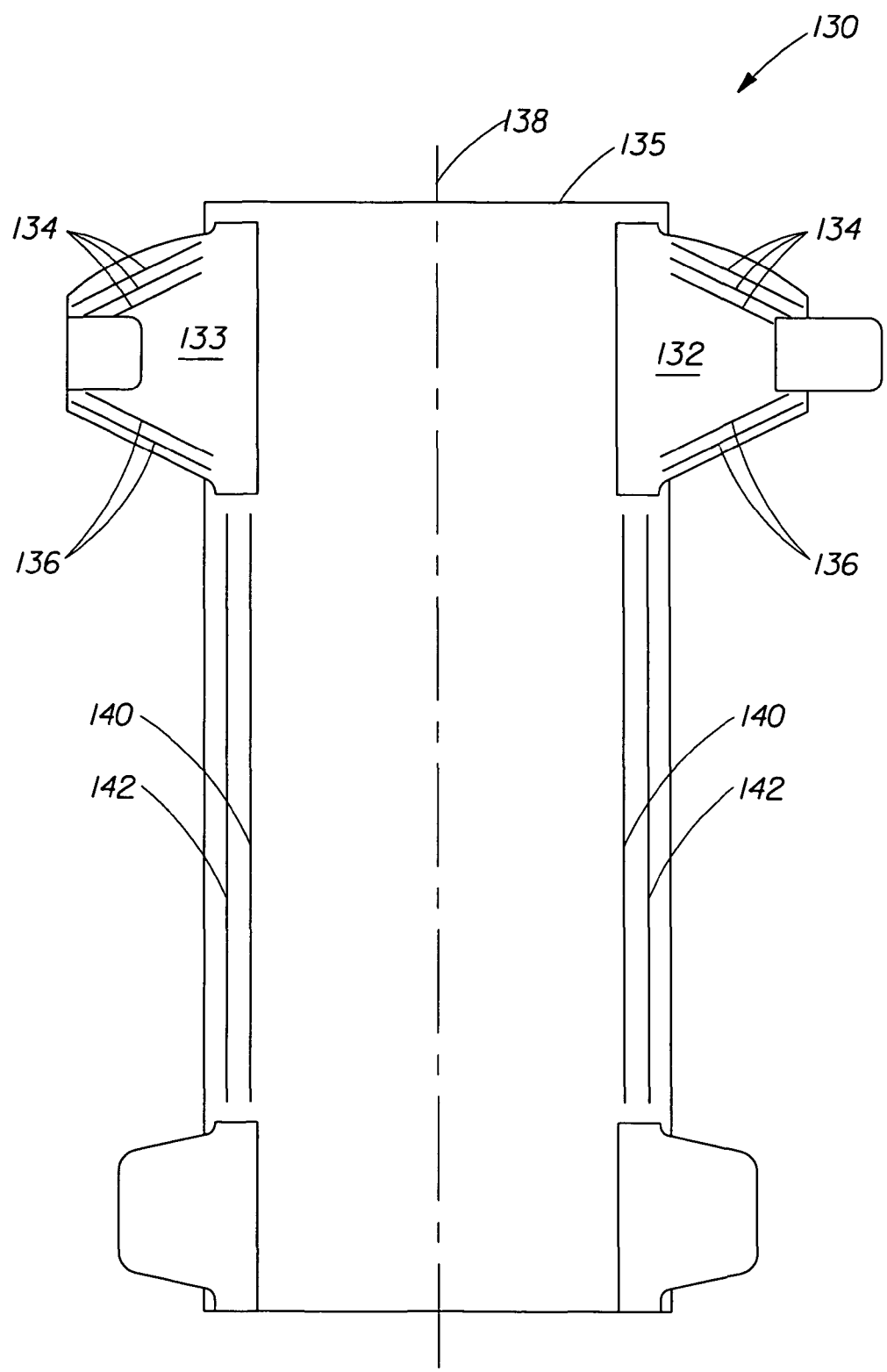
FIGS. 10A and 10B show yet another embodiment of the diaper of FIG. 1 in accordance with invention wherein plasto-elastic material is included in the ears and along the absorbent assembly for imparting the desired plastic and elastic properties to the diaper.
Figure 10B:
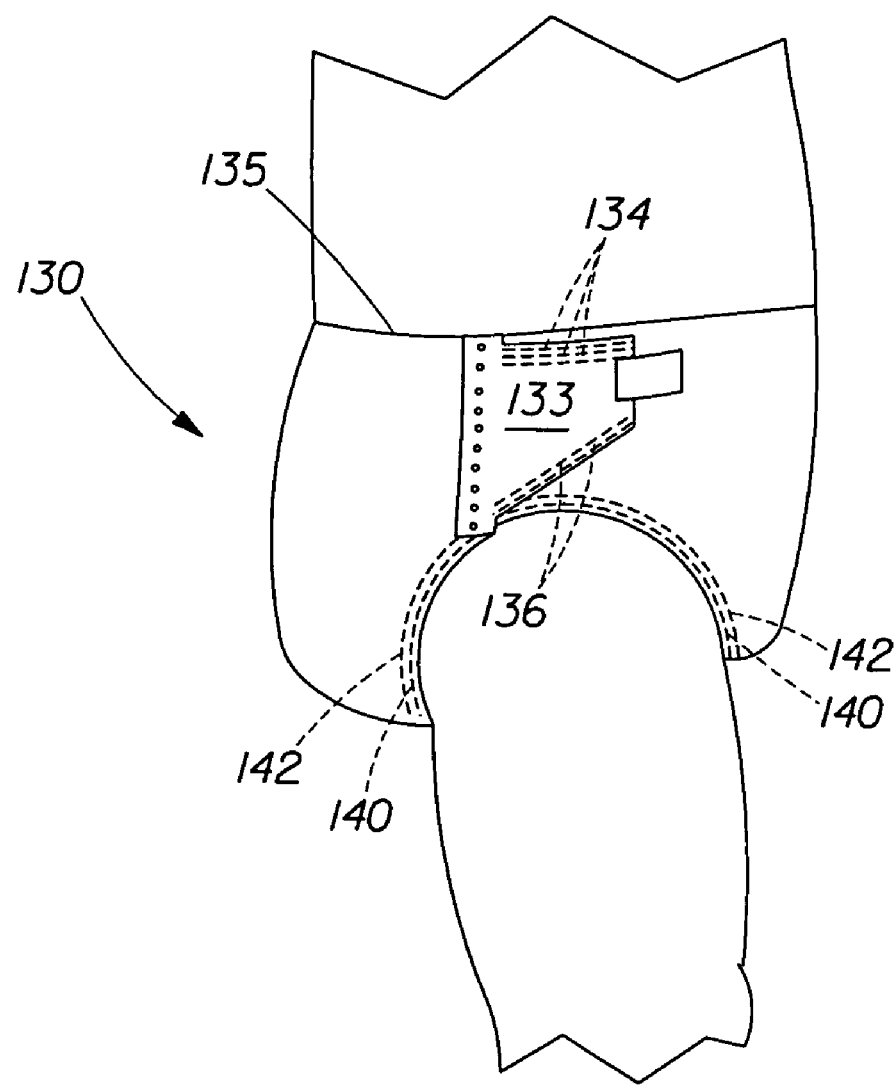

Referring to FIGS. 10A and 10B, a diaper 130 similar to diaper 10 and having a longitudinal centerline 138, a lateral centerline 139, a rear waist end 135 and a front waist end 137 is depicted in which the waist and thigh zones of the side panel 132 preferably comprise different stretch zones 134 and 136, varying in tension and/or angle as shown. Preferably, the side panel 134 stretch zone nearer the waist end 135 of diaper 130 may be oriented at an angle of about 0 to about minus 50 degrees from the lateral centerline 138, more preferably between about −5 degrees and about −30 degrees from the lateral centerline 138. Preferably, the stretch zone 136 may be oriented at an angle of about 0 to about plus 70 degrees from the lateral centerline 138, more preferably between about +20 degrees and about +60 degrees from the lateral centerline 138. One preferred side panel 132 stretch zone embodiment includes a stretch zone 134 oriented at about −10 to −20° from the lateral centerline 139 and a stretch zone 736 oriented at about +20° to +50° from the lateral centerline 139.

In certain preferred embodiments, at least one of the side panel stretch zones 136 may be aligned with the end of the outer leg cuff elastics 140, 142 in order to provide an effective extension of the leg cuff elastic, thereby encircling the leg 144 with a combination of stretch zone 136 and 140, 142 shown in FIG. 10B. Regardless of the specific construction, composition, or geometry, or stretch properties of the side panel 132, the stretch zones 134 and 136 in the waist and thigh areas are preferably capable of substantially independent action with respect to one another. Certain embodiments may include an additional side panel stretch zone functioning as a transition between the leg and thigh zones, i.e. a "transition zone". The transition zone may have distinctly different stretch properties than either the leg or waist zones and functions to decouple or separate the deformations induced in the leg and waist panels by a wearer's body shape and activity level, allowing them to act independently minimizing interaction (e.g., hindrance of one element by another) therebetween. In embodiments comprising a side panel transition zone, the transition zone may be substantially extensible to further promote independent action between the waist and thigh zones of the side panel, while still providing sufficient stretch to accommodate the relative movements of the waist and thigh zones while being worn by a wearer, controlling buckling and/or folding of the transition region.

Figure 11A:
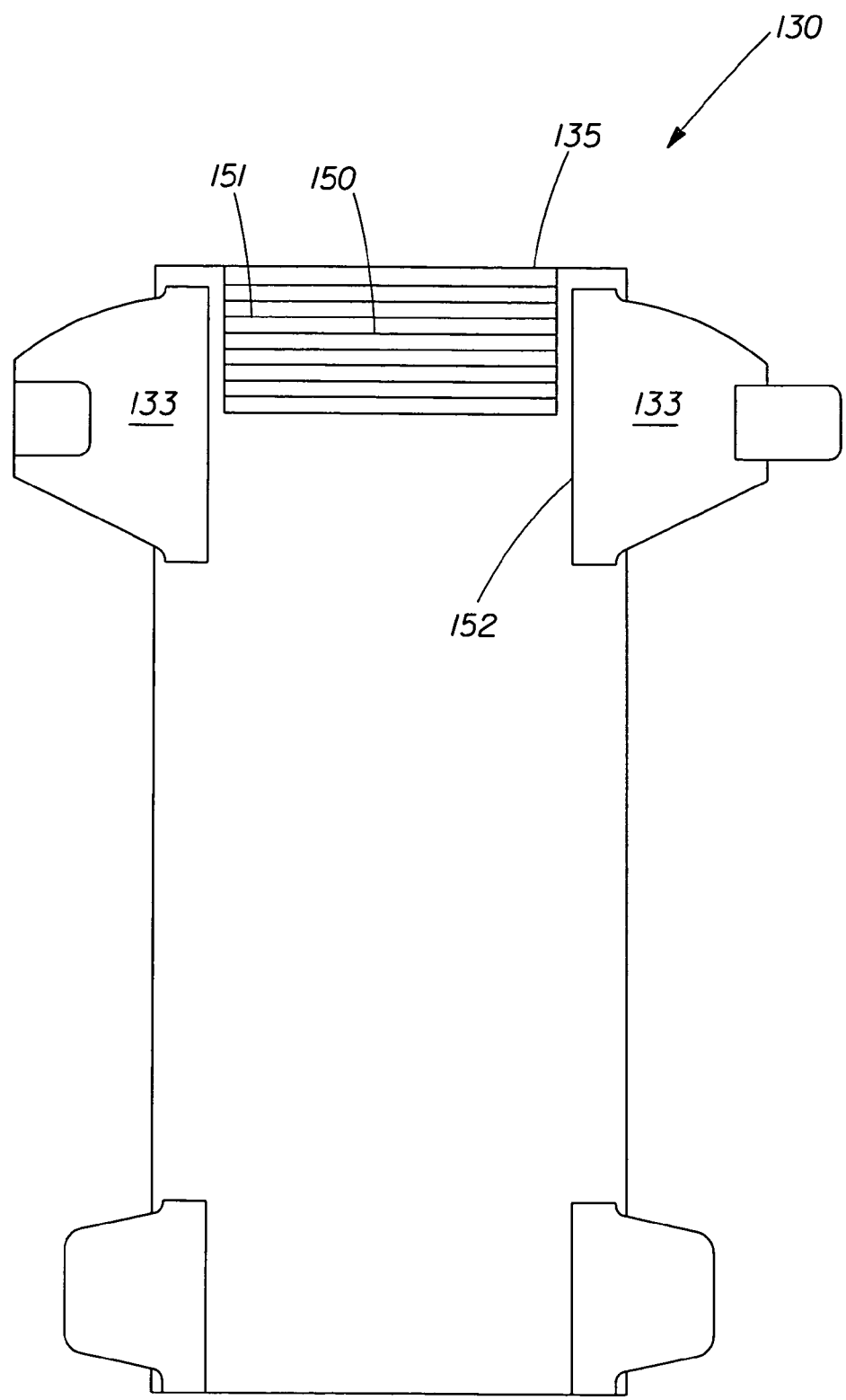
FIGS. 11A-D illustrate the diaper of FIG. 1 in which plasto-elastic material is disposed in a variety of locations to provide several alternative designs for improved wearer comfort and fit.
Figure 11B:
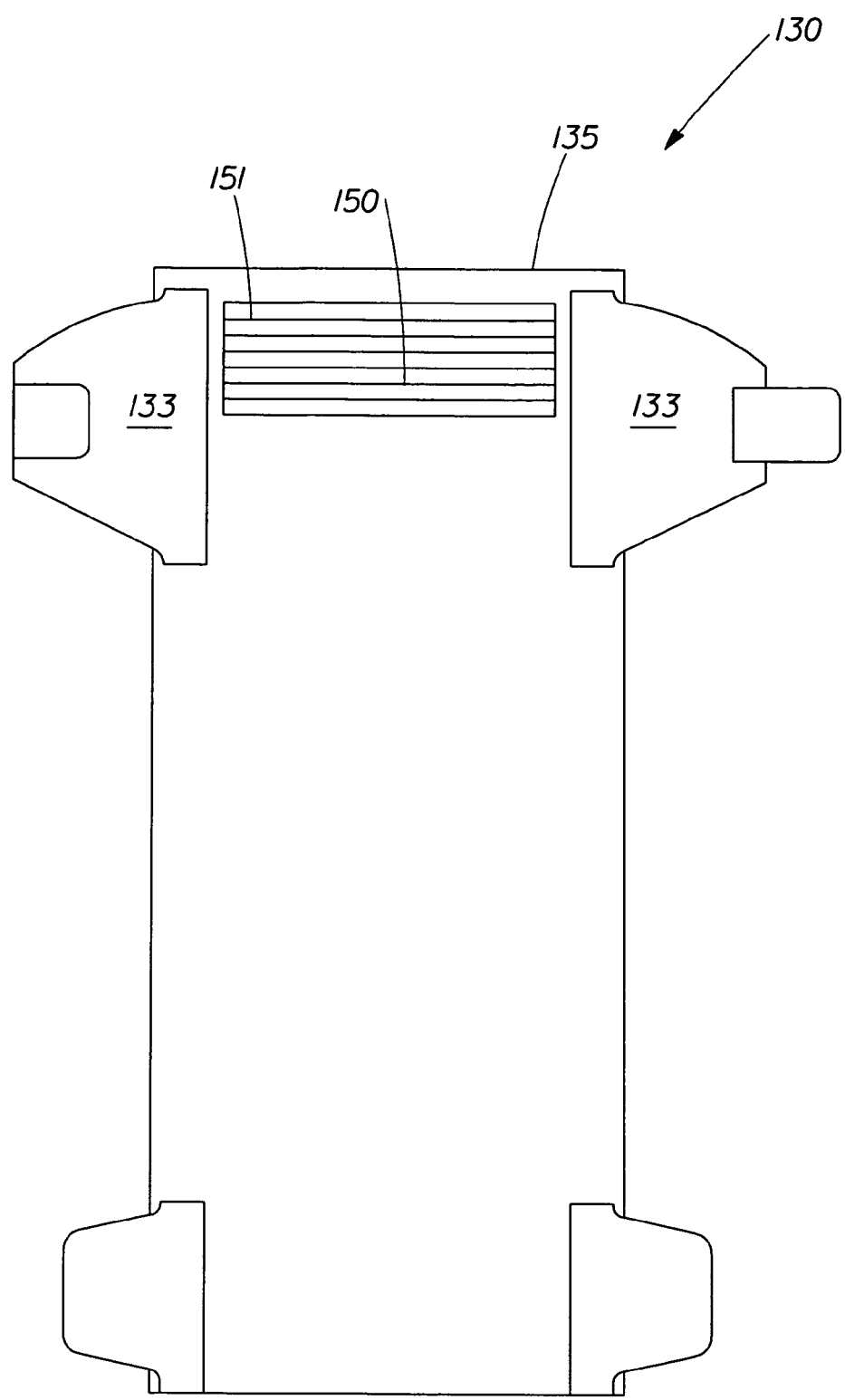
Figure 11C:
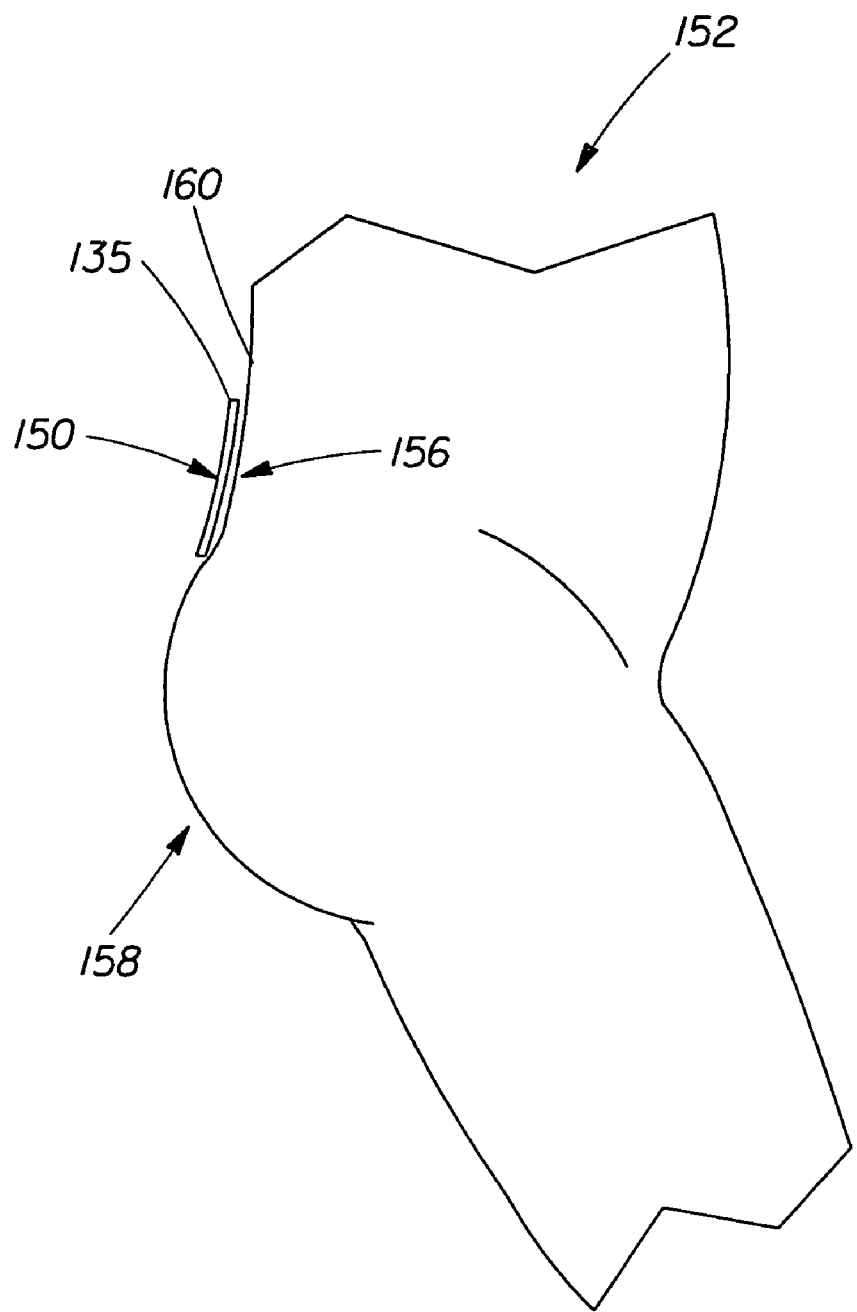

Referring to FIGS. 11A-D, at least one stretch zone 151 or array of stretch zones 150 may be included in the waist region of the diaper 130. The array 150 may have similar or varying degrees of elasticity or extensibility and may assume any geometry or orientation. For example, in FIG. 11A array 150 is located at the waist end 135 of diaper 130, whereas FIG. 11B shows another embodiment in which the array 150 is offset from waist end 135. It may be preferable to have the array 150 located generally in the lower back waist area as shown on a partial side view of wearer 152 in FIG. 11C. In this way, the maximum fit and comfort will be experienced by the wearer 152 as the tension is applied by the article to the wearer's body at or immediately above the convexity of the buttocks (i.e., the "buttocks shelf"), contributing to the overall anchoring capability of the article (i.e., its ability to resist sagging).

Figure 11D:
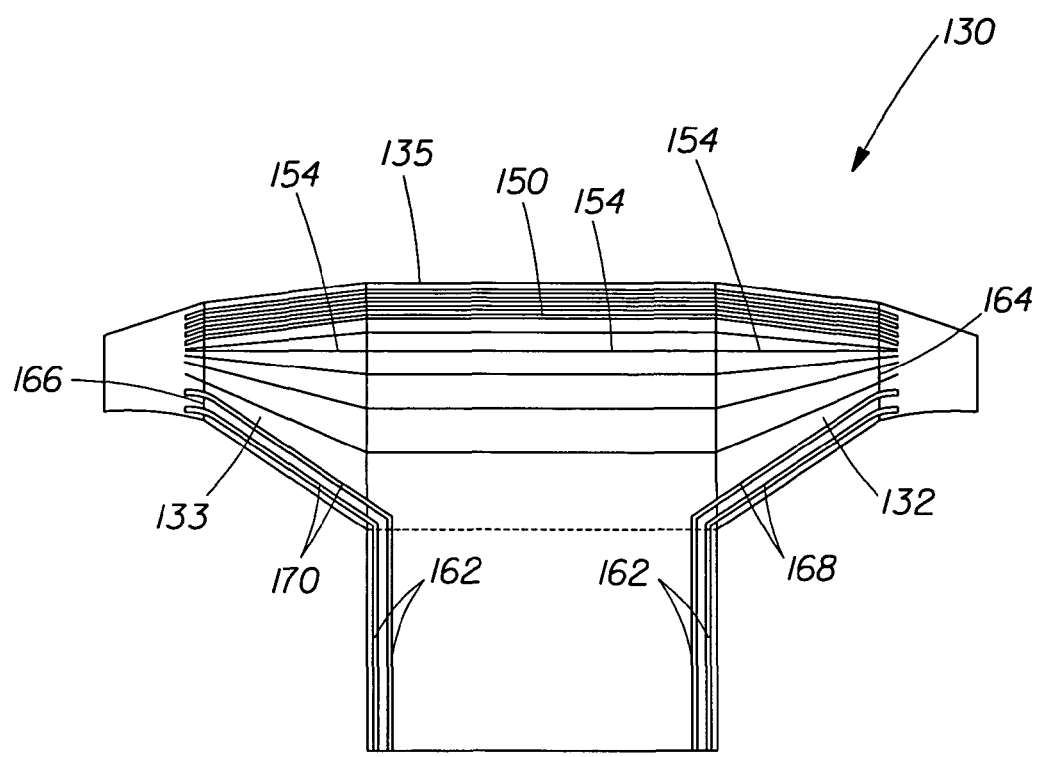

In certain preferred embodiments as shown in the partial plan view of diaper 130 in FIG. 11D, array 150 comprises a plurality of stretch zones 154 that extend into side panels 132, 133. These stretch zones 154 have a high localized resistive elastic forces or a "high tension" and are aligned with the waist end 135. The high-tension stretch zones 154 may be adjacent the waist end 135 or may be disposed inboard thereof. Typically, the high-tension stretch zones 154 are disposed between about zero and 30 mm from the waist end 135 of the diaper 130. Preferably, the high-tension stretch zones 154 are disposed less than about 20 mm from the waist end 135. Generally, the high-tension stretch zones 154 may correspond to an area 156 on the wearer 152 body immediately above or at the upper curvature of the buttocks 158 where the high-tension stretch zones 154 (or array 150) functions to provide additional anchoring capability for the diaper 152 by applying a normal force to the geometric "shelf" created by the buttocks 158. The high tension stretch zones 154 comprising array 150 additionally hold the waist end 135 of the diaper 152 against the wearer's back 160 preventing back waist gapping.

In embodiments comprising an array 150 of stretch zones 154 at or near the waist end 135 of diaper 130 and extending through multiple regions of the back waist and crotch of the article, the remaining area of the waist end 135 may have either a lower elastic resistive force, may be primarily extensible, or may comprise areas with either property. In any case, this waist end 135 area (i.e., the area not including the stretch zones 150 or 154) may be a low-tension zone.

Referring to FIG. 11D, stretch zones 162, which comprise a portion of a leg gasketting feature, may be substantially aligned with the longitudinally outboard edges 164 and 166 of side panels 132 and 133, respectively. Optionally, transition stretch zones 168 and 170 may be disposed intermediate stretch zones 154 and 162. The stretch zone 154 may provide a primary anchoring function and stretch zones 162, 168 and 170 may provide a dynamic leg motion accommodation function. While stretch zones 154 and 162 may be preferably primarily elastic, stretch zones 168 and 170 may be primarily extensible so as to act as a transition zone as described above.

Preferably, diaper 130 also comprises at least one extensible stretch zone so as to provide adequate coverage of the buttocks 158 (not shown in FIGS. 11A-D, see FIGS. 14A, B), conform to a wearer's shape, and relieve stress in the transition region between the crotch as it goes between the wearer 152 (FIG. 11C) legs and the waist end 135 region. As described previously, side panels 132 and 133 may comprise distinct stretch zones 154, 162, 168 and 170 having different functions and may be single stretch zones having different properties throughout the stretch zone or have physical delineations between stretch zones 154, 162, 168 and 170 such as slits, holes, or other deformation. However, stretch zones 154 and 162 preferably comprise stretch zones, or arrays of stretch zones, having different properties, geometry, and/or dimensions from each other.

Figure 12:
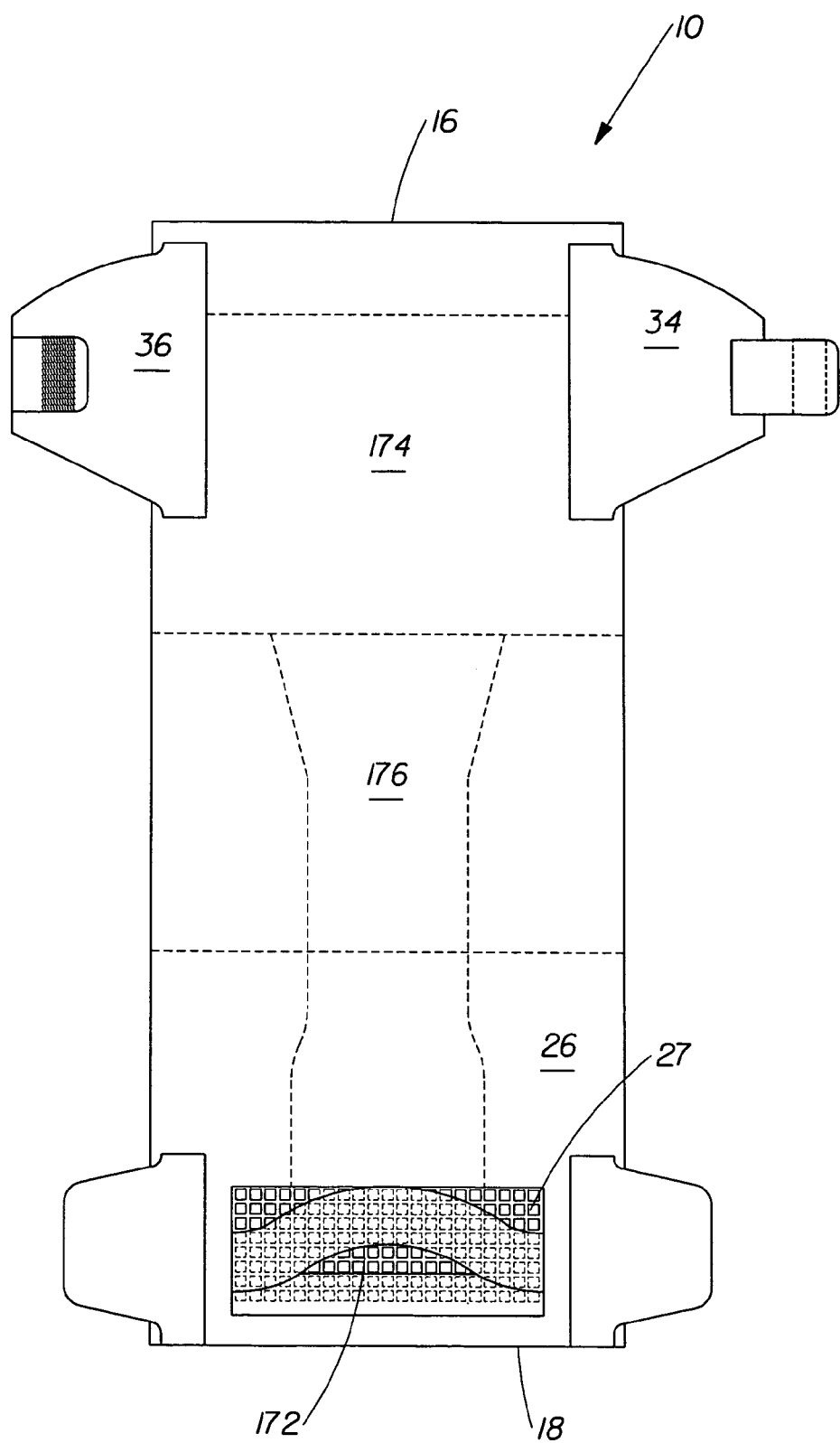
FIG. 12 is a plan view of a diaper in accordance with the invention in which plasto-elastic material is disposed in the diaper ears and the front waist portion.

Referring to FIG. 12, another embodiment of diaper 10 is depicted in which the front waist region 26 may comprise at least one stretch zone 172 The function of stretch zone 172 is to dynamically accommodate the contraction and expansion cycles of the wearer's abdomen as the wearer moves and/or changes position, preventing front waist sagging. The stretch zone 172 is preferably substantially aligned with the front waist end 18 of the diaper 10. In closable versions of diaper 10 including a fastening landing zone 27 disposed in or near the front waist end 18, the landing zone 27 may be shaped in a configuration presenting a concavity to the front waist end 18 of the diaper 10. In these embodiments, stretch zone 172 may at extend into the landing zone 27 concavity 172 as shown in FIG. 12.

While the buttocks region 174 located in the back waist region in proximity to the crotch region as shown on diaper 10 may comprise either elastic or extensible stretch zones, or a combination thereof, in preferred embodiments, the buttocks region 174 may be primarily extensible in order to accommodate the largest wearer circumference (i.e., the buttocks) and the volume of the absorbent core 176 depicted in dashed lines, allowing the buttocks region 174 to have a lower on-wearer tension than the rear waist end 16 region. The buttocks region 174 may have stretch zones with extensibility that allows for a smoother geometric transition from the constricted absorbent care 176 between the wearer's legs to the side panels 34 and 36 which may have stretch zones as described in FIG. 11D for anchoring. The buttocks region 174 preferably may elongate further than the waist end 16 region to accommodate the wearer's anatomic shape.

Figure 13:
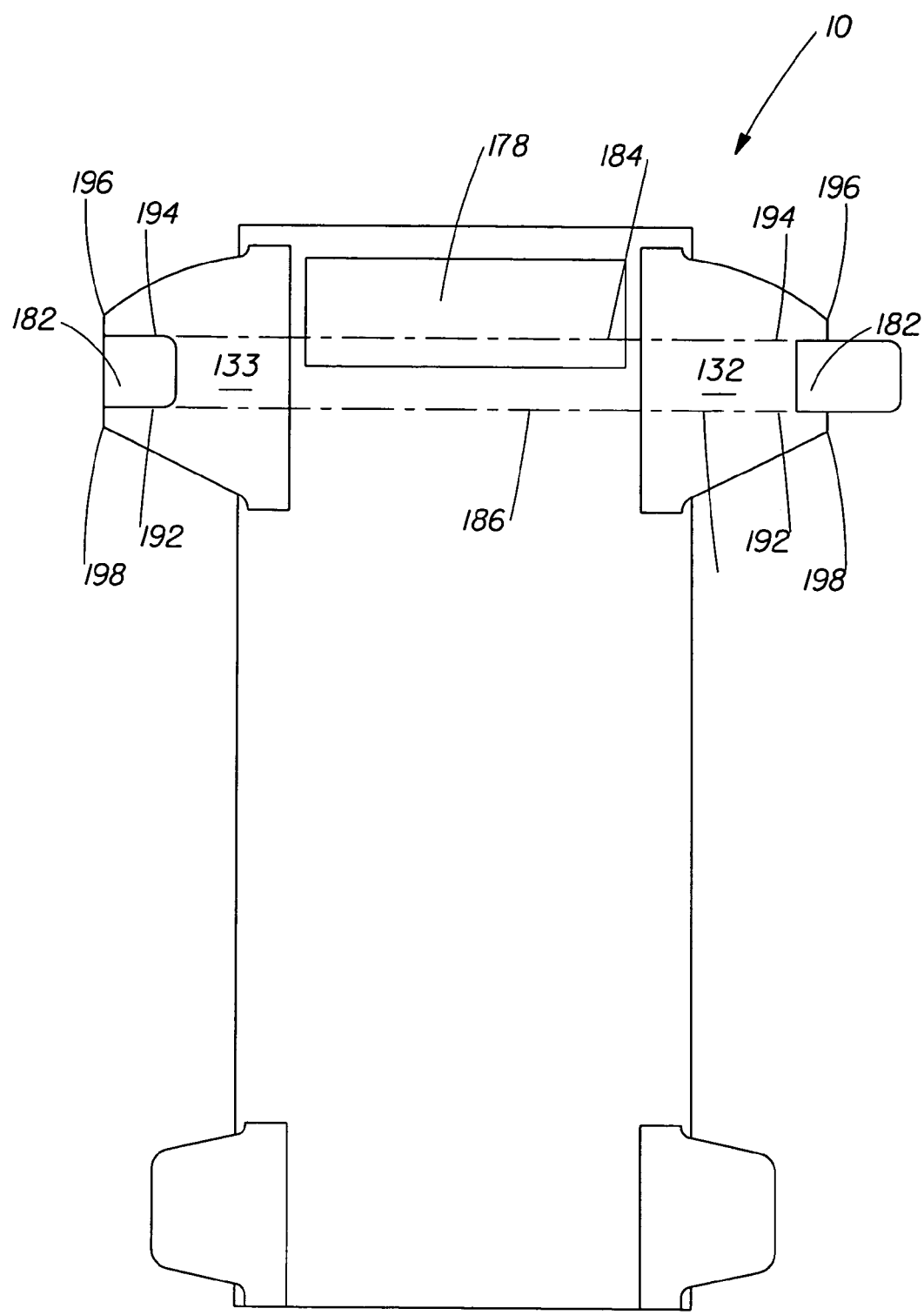
FIG. 13 is a plan view of a diaper in accordance with the invention in which the plasto-elastic material is disposed in the rear waist portion such that at least a portion of the plasto-elastic material is longitudinally aligned with the diaper ears.

Referring to FIG. 13, another embodiment of diaper 130 is shown in which region 178 is provided with a stretch zone or array of stretch zones that lie adjacent the rear waist region. This region may be preferably aligned with the side panels 132 and 133 and/or the fasteners 180 and 182 disposed on side panels 132 and 133 in order to create a substantially continuous line of tension around the waist to promote conforming sustained fit. As shown in FIG. 13, the stretch zone 178 preferably at least partially overlaps one of the two imaginary lines 184 and 186 that connect the longitudinally outboard edges 188, 190 and 192, 194 of either fasteners 180 and 182, respectively. In embodiments in which diaper 130 does not include fasteners 180 and 182, for example in diaper pant 70 of FIG. 4, imaginary lines 184 and 186 may connect the narrowest outboard point edges 196 and 198 of side panel 133 and its opposing outboard point edges 200 and 202 on side panel 132. In embodiments which include a stiffening element that is wider than the fastener (not shown), the separation of the imaginary lines is defined by the longitudinal length of the stiffening element.

Figure 14A:
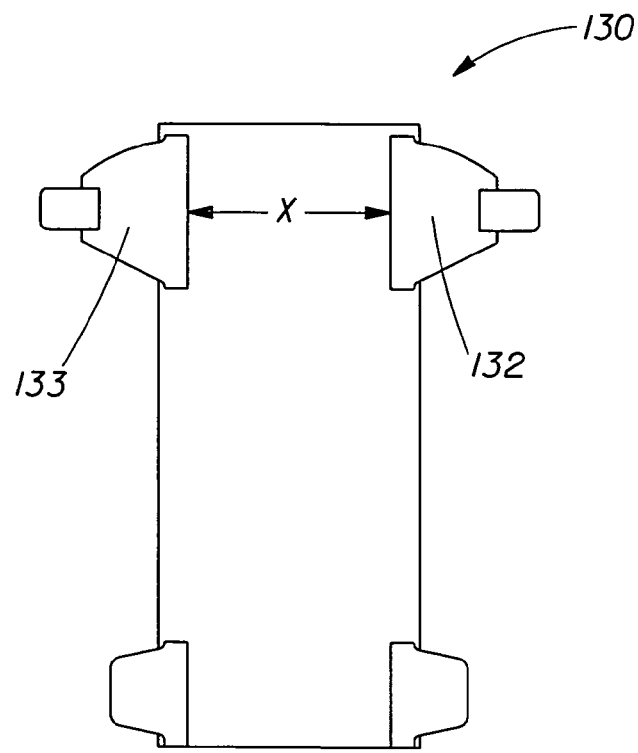
FIGS. 14A and 14B are plan views of a diaper in accordance with the invention in which an exemplary amount of size increase is shown after the initial application of pull, stretch or strain to the diaper ears.
Figure 14B:
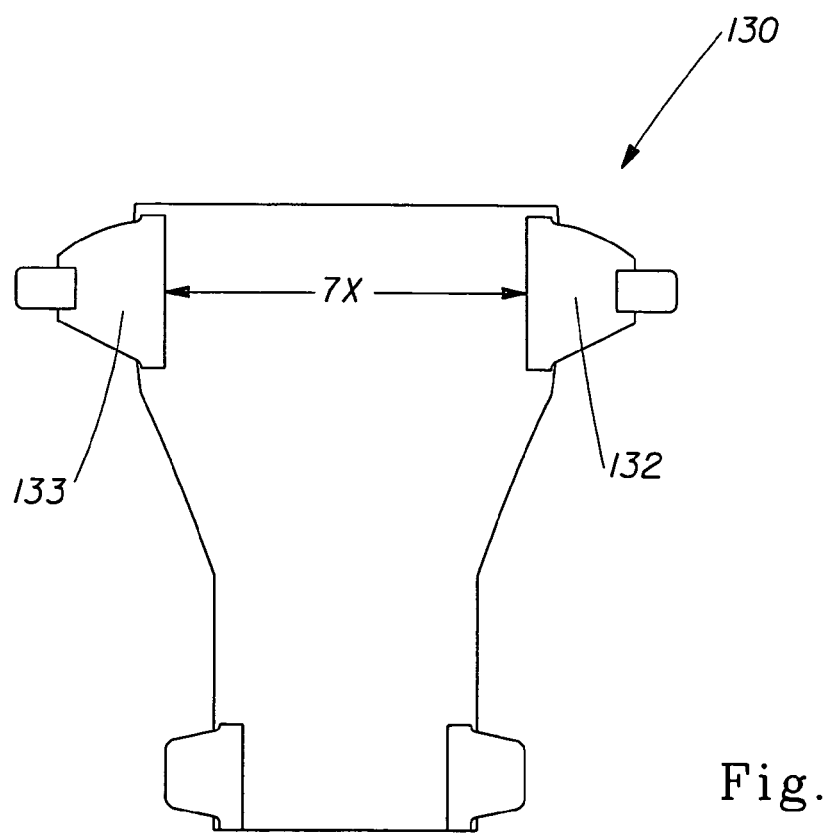

FIG. 14A show diaper 130 before the initial pull or stretch, and FIG. 14B show diaper 130 after the initial stretch or pull to exemplify twice its original size extensible capability. The diaper 130 embodiment of FIGS. 14A and 14B may employ any one or more of the stretch zone options previously discussed.

Figure 15:
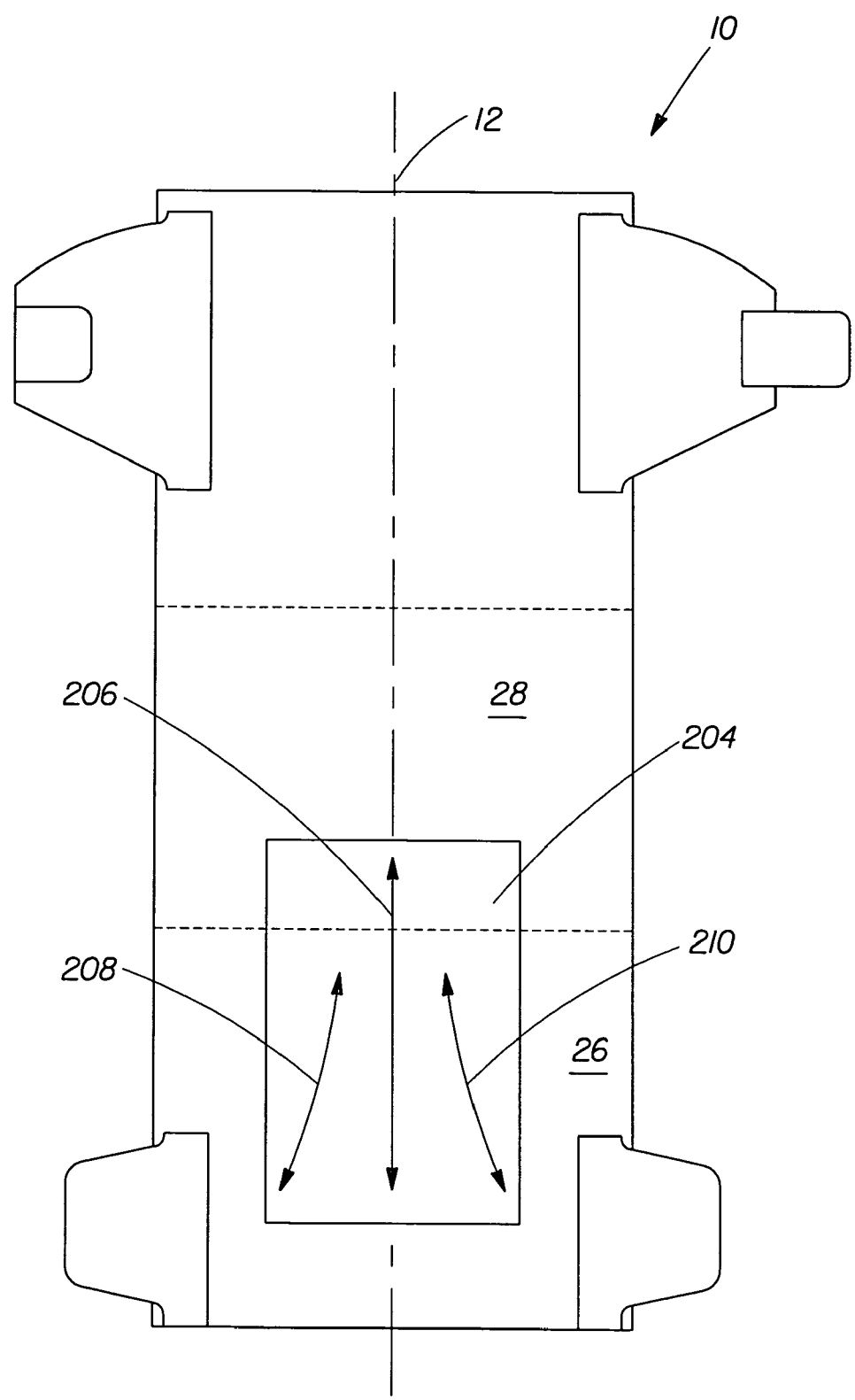
FIG. 15 is a plan view of a diaper having plasto-elastic material in the front crotch portion in accordance with the invention.

Referring to FIG. 15, a stretch zone 204 is shown on diaper 10 in the front crotch region 28 spanning into the front waist region 26. The stretch zone 204 may be primarily oriented in the longitudinal direction of the diaper 10 allowing the user to adjust the longitudinal dimension by arrow 206, or "rise", of the diaper to better fit larger or taller wearers. The stretch zone 204 may be primarily extensible in order to avoid large residual contractive forces that might pull the front of diaper 10 down, resulting in sagging. Preferably, the area of greatest extension is substantially aligned with and overlapping the longitudinal centerline 12. Stretch zone 204 may also comprise stretch zones laterally outboard of and at an angle to the longitudinal centerline 12 and diverging toward the front corners of diaper 10 as shown by arrows 208 and 210 in FIG. 15. These lines or arcs of tension may be primarily elastic so as to provide suitable suspension for the absorbent core and wearers' waist held therein by "connecting" these loads to the anchoring zones of the article via suitable lines, or "paths" of tension. Alternatively, these "load distribution elements" may comprise lines, arcs, bands, or other geometric regions of inextensibility in the surrounding areas of crotch region 28 and front waist region 26 and may extend to accommodate the wearer's rise, while the outboard inextensible load distribution elements provide support for waste load.

Figure 16:
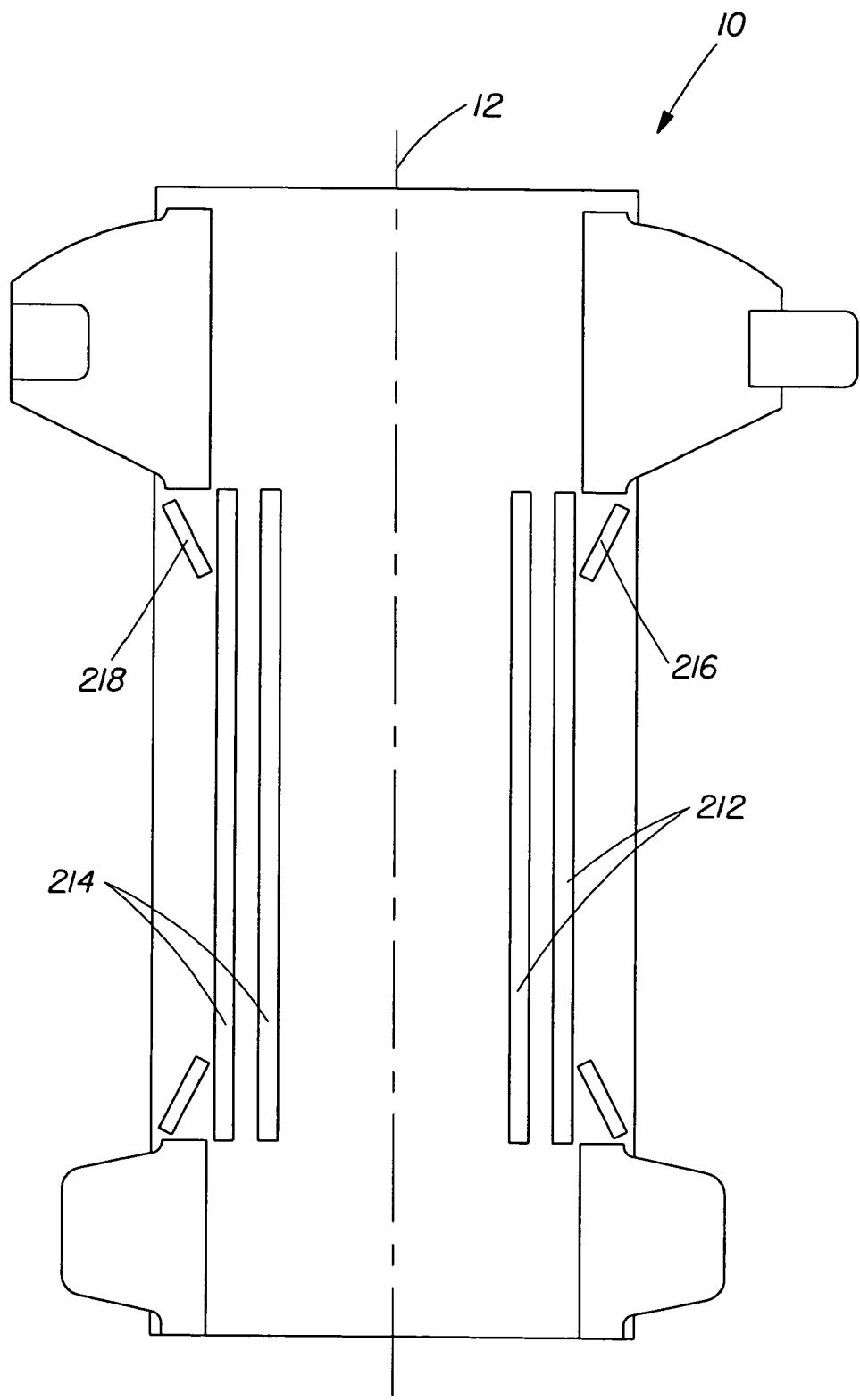
FIG. 16 is another plan view of a diaper in which plasto-elastic material is disposed along the lateral portions of a diaper in order to provide the desired plastic and elastic properties in the leg openings.

Referring to FIG. 16, another embodiment of diaper 10 is shown in which leg regions 30 and 32 may stretch zones 212 and 214. Preferably, stretch zones 212 and 214 are substantially aligned in the longitudinal direction and are highly elastic. Optionally, stretch zones 212 and 214 may be included that may be curvilinear or at an angle to the longitudinal centerline 12. Portions of the leg regions 30 and 32 may comprise one or more additional extensible stretch zones 216 and 218 that are oriented at an angle to the longitudinal centerline 12 of diaper 10. Typically, stretch zones 216 and 218 may be at an angle of about 45 degrees to about 90 degrees from the longitudinal centerline 12.

Diaper Component Description Applicable to All Embodiments of Present Invention

All of the embodiments in FIGS. 1-13 have diaper components which may take any one or more of the materials, designs, and methods of assembly described hereinafter without departing from the scope of the present invention. While any of the article components may be assembled in a variety of well known configurations, exemplary diaper configurations are described generally in U.S. Pat. Nos. 3,860,003; 5,151,092; and 5,221,274; and 5,554,145; 5,569,234; 5,580,411; and 6,004,306.

Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Exxon Chemical Co., of Bay City, Tex., under the designation EXXAIRE, and monolithic films such as manufactured by Clopay Corporation, Cincinnati, Ohio under the name HYTREL blend P18-3097 Some breathable composite materials are described in greater detail in U.S. Pat. Nos. 6,187,696; 5,938,648; 5,865,823; and 5,571,096.

The article may include a structural elastic-like film web is an extensible material that exhibits an elastic-like behavior in the direction of elongation without the use of added elastic materials and is described in more detail in U.S. Pat. No. 5,518,801. In alternate embodiments, the backsheets may comprise elastomeric films, foams, strands, or combinations of these or other suitable materials with nonwovens or synthetic films.

Exemplary absorbent structures for use as the absorbent core are described in U.S. Pat. Nos. 4,610,678; 4,673,402; 4,834,735; 4,888,231; 5,137,537; 5,147,345; 5,342,338; 5,260,345; 5,387,207; and 5,625,222.

Suitable absorbent and nonabsorbent sublayers are described in European Patent Application No. EP 0 847 738 A1 and U.S. Pat. No. 5,941,864. Further, the sublayer, or any portion thereof, may include or be coated with a lotion or other known substances to add, enhance or change the performance or other characteristics of the element.

Some exemplary surface fastening systems are disclosed in U.S. Pat. Nos. 3,848,594; B1 4,662,875; 4,846,815; 4,894,060; 4,946,527; the herein before referenced U.S. Pat. Nos. 5,151,092; and 5,221,274. An exemplary interlocking fastening system is disclosed in co-pending U.S. application Ser. No. 09/143,184 entitled "Absorbent Article Fastening Device" in the names of Kline et al. filed on Aug. 8, 1998. The fastening system may also: provide a means for holding the article in a disposal configuration as disclosed in U.S. Pat. No. 4,963,140; include primary and secondary fastening systems, as disclosed in U.S. Pat. No. 4,699,622; means to reduce shifting of overlapped portions or to improve fit as disclosed in U.S. Pat. No. 5,242,436. means to resist gapping at a wearer's belly as disclosed in U.S. Pat. Nos. 5,499,978 in U.S. Pat. No. 5,507,736 and in U.S. Pat. No. 5,591,152.

Suitable training pants and pull-on diapers are disclosed in U.S. Pat. Nos. 5,246,433; 5,569,234; 6,120,487; 6,120,489; 4,940,464; and 5,092,861.

Examples of diapers with elasticized side panels are disclosed in U.S. Pat. Nos. 4,857,067; 4,381,781; 4,938,753; the herein before referenced U.S. Pat. Nos. 5,151,092; 5,221,274; 5,669,897; and 6,004,306.

U.S. Pat. No. 3,860,003 describes a disposable diaper which provides a contractible leg opening having a side flap and one or more elastic members to provide an elasticized leg cuff (a gasketting cuff). U.S. Pat. Nos. 4,808,178 and 4,909,803 describe disposable diapers having "stand-up" elasticized flaps (barrier cuffs) which improve the containment of the leg regions. U.S. Pat. Nos. 4,695,278 and 4,795,454 describe disposable diapers having dual cuffs, including gasketting cuffs and barrier cuffs.

Embodiments of the present invention may also include pockets for receiving and containing waste, spacers which provide voids for waste, barriers for limiting the movement of waste in the article, compartments or voids which accept and contain waste materials or any combinations thereof. Examples of pockets and spacers for use in absorbent products are described in U.S. Pat. Nos. 5,514,121; 5,171,236; 5,397,318; 5,540,671; 6,168,584; 5,306,266; and 5,997,520. Examples of compartments or voids are disclosed in U.S. Pat. Nos. 4,968,312; 4,990,147; 5,062,840; and 5,269,755. Examples of suitable transverse barriers are described in U.S. Pat. Nos. 5,554,142; 6,010,490; and 5,653,703. Examples of other structures especially suitable for management of low viscosity feces are disclosed in U.S. Pat. Nos. 5,941,864; 5,977,430 and 6,013,063.

The diaper 10 of FIG. 1 is preferably applied to a wearer by positioning one of the waist regions under the wearer's back and drawing the remainder of the diaper between the wearer's legs so that the other waist region is positioned across the front of the wearer. The fastener elements are then used by the caregiver to join the front and rear waist regions so as to encircle the wearer's waist. The elasticized side panels will typically be extended and tensioned during this operation so as to conform to the size and shape of the wearer. A pant, such as that shown in FIG. 6, may be placed in position on the wearer by inserting the wearer's legs into the leg openings and sliding the pant into position about the wearer's lower torso.

EXAMPLES

Comparative Example 1

This example describes film formation from two resins of the prior art: an experimental grade of ADFLEX 7573 (a reactor blend of an ethylene-based elastomer and polypropylene available from Basell Polyolefins of Wilmington, Del.) (1-1); an isotactic polypropylene with stereoerrors along the polymer chain as disclosed in U.S. Pat. No. 6,555,643 (1-2); a high-performance blend typically used in diaper stretch components comprising a styrenic block copolymer available from Kuraray Co. Ltd. of Tokyo, Japan as Septon 4033 (1-3); an elastomeric polypropylene as is available from Exxon Mobil Chemical of Huston, Tex. as VISTAMAXX 1100 (1-4); and two blends of a very low density polyethylene (EXACT 4049 from Exxon Mobil of Huston, Tex.) and a linear low density polyethylene (LL6201 from Exxon Mobile Chemical of Huston, Tex.) where ID 1-5 is 85% VLDPE/15% LLDPE and 1-6 is 70% VLDPE/30% LLDPE. Tables 1 and 2 list film properties.

TABLE 1

| Composition ID | Prestrain Temperature (° C.) | Specimen width (mm) | Film basis weight (g/m$^2$) | Initial load @ 50% strain[1] (N) | Final load @ 50% strain[1] (N) | Force Relax. (10 hrs) (%) |
|---|---|---|---|---|---|---|
| 1-1 | 23 | 12.7 | 97 | 3.44 | 1.49 | 57 |
| 1-2 | 23 | 12.7 | 141 | 1.06 | 0.54 | 49 |
| 1-3 | 23 | 15.9 | 179 | 0.61 | 0.44 | 28 |
| 1-4 | 23 | 19.0 | 151 | 0.99 | 0.40 | 59 |
| 1-5 | 23 | 12.7 | 143 | 2.27 | 0.98 | 57 |
| 1-6 | 23 | 12.7 | 103 | 2.24 | 1.14 | 49 |

[1]Normalized to 150 g/m$^2$ and 6.4 mm width

TABLE 2a

| | | 1st Cycle (200%, RT) | | | 2nd Cycle (50%, R.T.) | | |
|---|---|---|---|---|---|---|---|
| Blend ID | Basis Weight g/m$^2$ | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 1-1 | 111 | 6.88 | 87.9 | 6.36 | 51.4 | 0.25 | 15.3 |
| 1-2 | 154 | 2.74 | 3.9 | 1.24 | 18.8 | 0.64 | 6.7 |
| 1-3 | 128 | 1.13 | 5.4 | 0.64 | 7.5 | 0.39 | 4.0 |
| 1-4 | 148 | 1.75 | 13.6 | 0.95 | 17.4 | 0.45 | 6.7 |

TABLE 2b

| | | 1st Cycle (300%, RT) | | | 2nd Cycle (200%, R.T.) | | |
|---|---|---|---|---|---|---|---|
| Blend ID | Basis Weight | Stress @ 200% Prestrain | % Set after 1st Cycle | Stress @ 50% | % Force Relaxation @ 50% | Stress @ 30% Unload | % Set after 2nd Cycle |
| 1-5 | 180 | 3.54 | 74.2 | 4.15 | 29.8 | * | >30% |
| 1-6 | 168 | 4.14 | 86.5 | 5.12 | 32.0 | * | >30% |

*Stress too low to measure

As can be seen: 1) the polyethylene-containing blends typically have a relatively high stress at both 200% and 50% elongations (related to stiffness), 2) a high force relaxation after a second elongation cycle (>15%) and, sometimes, 3) negligible stress at 30% elongation during the unload of the second cycle and/or a high level of additional set after a second loading cycle.

Example 2

This example illustrates the possibility of modifying the tensile properties of a commercial elastomeric polypropylene via the addition of a commercial soft, deformable polyolefin-based material.

The following materials were compounded in a batch mixer available from Haake Polylab of Newington, N.H. Fifty gram batches were processed for about 6 min at 170° C. Commercially available antioxidants were also added to the mix at a low level (<1%) to help protect the blend from thermal/oxidative degradation. The following compositions (all values in wt. percent) were prepared according Table 3

TABLE 3

| Blend ID | Elastomeric Polypropylene[1] | Polyolefin Material[2] | LLDPE[3] | VLDPE[4] |
| --- | --- | --- | --- | --- |
| 2-1 | 100 | 0 | 0 | 0 |
| 2-2 | 60 | 40 | 0 | 0 |
| 2-3 | 60 | 30 | 10 | 0 |
| 2-4 | 60 | 30 | 0 | 10 |
| 2-5 | 40 | 60 | 0 | 0 |
| 2-6 | 40 | 45 | 15 | 0 |
| 2-7 | 40 | 45 | 0 | 15 |

[1]Elastomeric polypropylene as is available from Exxon Mobil Chemical of Huston, TX as VISTAMAXX 1100.
[2]PARAFILM M is a polyolefin laboratory film commercialized by American National Can of Chicago, IL. The film was cut into pieces prior to being added to the batch mixer.
[3]Linear low Density polyethylene (MI = 50 g/10 min, Density = 0.926 g/cm$^3$,) as is available from Exxon Mobil Chemical of Huston, TX as LL6201.
[4]Very low density polyethylene (MI = 4.5 g/10 min; Density = 0.873 g/cm$^3$) as is available from Exxon Mobil Chemical of Huston, TX as EXACT 4049.

Compression-molded film samples were prepared using a Carver press (Available from Carver, Inc. of Wabash, Ind.) using the following steps:
1. Place a Teflon® template (A Teflon® sheet with the center area cut away to define the sample area). The thickness of the sheet determines the thickness of the sample.) on a 0.005" thick Teflon® sheet. Place composition to be formed onto the press, in the open area of the template. Cover with a second 0.005" thick Teflon® sheet.
2. Place the Teflon® sheets/composition "sandwich" between heated (200° C.) platens of the Carver Press and slowly load to 5,000 pounds of pressure. Wait 30 seconds.
3. Increase pressure to 12,000 lbs and wait 60 seconds.
4. Release pressure, rotate the Teflon® sheets/composition "sandwich" 180° and load to 12,000 lbs. Wait 30 seconds and release pressure.
5. Immediately remove the Teflon® sheets/composition "sandwich" and cool it between room-temperature metal plates.
6. If the film that has been formed does not readily release from the Teflon®, place in a freezer, wait 5 minutes, and peel film from Teflon®.

The film samples were allowed to age for 24 hrs before being subjected to mechanical testing. Force relaxation (Table) and hysteresis testing (Tables 5 and 6) was carried out according to the methods described above and the data are shown in the following tables (A minimum of two specimens was analyzed for each reported value):

TABLE 4

| Blend ID | Prestrain Temperature[1,2] (° C.) | Specimen width (mm) | Film basis weight (g/m$^2$) | Initial load @ 50% strain[3,4] (N) | Final load @ 50% strain[3,4] (N) | Force Relax. (10 hrs) (%) |
| --- | --- | --- | --- | --- | --- | --- |
| 2-1 | 23 | 19 | 151 | 0.99 | 0.40 | 59 |
| 2-2 | 23 | 19 | 131 | 0.82 | 0.23 | 71 |
| 2-2 | 40 | 19 | 120 | 0.54 | 0.19 | 65 |
| 2-2 | 40[3] | 13 | 135 | 0.48 | 0.16 | 66 |
| 2-3 | 23 | 19 | 104 | 0.87 | 0.25 | 70 |
| 2-4 | 23 | 13 | 124 | 0.89 | 0.26 | 71 |
| 2-5 | 23 | 19 | 109 | 0.58 | 0.14 | 77 |
| 2-5 | 40 | 13 | 97 | 0.46 | 0.14 | 70 |
| 2-6 | 23 | 19 | 106 | 1.05 | 0.33 | 69 |
| 2-7 | 23 | 13 | 104 | 1.09 | 0.35 | 68 |

[1]Temperature at which prestrain step was conducted.
[2]Prestrained to 300% instead of 200%
[3]Normalized to 150 g/m$^2$ and 6.4 mm width
[4]Strained to 50% before reaching temperature equilibrium in environmental chamber

TABLE 5

| | | 1st Cycle (200%, RT) | | | 2nd Cycle (50%, R.T.) | | |
| --- | --- | --- | --- | --- | --- | --- | --- |
| Blend ID | Basis Weight g/m$^2$ | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 2-1 | 148 | 1.75 | 13.6 | 0.95 | 17.4 | 0.45 | 6.7 |
| 2-2 | 156 | 1.45 | 30.1 | 0.84 | 26.7 | 0.21 | 7.8 |

TABLE 5-continued

| | | 1st Cycle (200%, RT) | | | 2nd Cycle (50%, R.T.) | | |
|---|---|---|---|---|---|---|---|
| Blend ID | Basis Weight g/m$^2$ | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 2-3 | 106 | 2.12 | 24.4 | 1.00 | 26.4 | 0.25 | 7.9 |
| 2-4 | 135 | 2.04 | 22.4 | 1.02 | 24.5 | 0.31 | 7.6 |
| 2-5 | 117 | 1.25 | 43.4 | 0.81 | 31.7 | 0.13 | 9.6 |
| 2-6 | 104 | 2.29 | 48.1 | 0.60 | 34.7 | 0.08 | 10.0 |
| 2-7 | 110 | 2.50 | 46.6 | 1.34 | 24.5 | 0.26 | 7.9 |

TABLE 6[1]

| | | 1st Cycle (300%, RT) | | 2nd Cycle | |
|---|---|---|---|---|---|
| Blend ID | Basis Weight g/m$^2$ | Stress @ 300% Prestrain MPa | % Set after 1st Cycle % | Stress @ 200% MPa | (200%, R.T.) % Force Relaxation @ 200% % |
| 2-1 | 132 | 1.92 | 19.6 | 1.50 | 18.3 |
| 2-2 | 161 | 1.69 | 46.5 | 1.82 | 32.7 |
| 2-3 | 108 | 2.55 | 36.8 | 2.26 | 31.7 |
| 2-4 | 134 | 2.53 | 37.6 | 2.36 | 28.8 |

TABLE 6[1]-continued

| | | 1st Cycle (300%, RT) | | 2nd Cycle | |
|---|---|---|---|---|---|
| Blend ID | Basis Weight g/m$^2$ | Stress @ 300% Prestrain MPa | % Set after 1st Cycle % | Stress @ 200% MPa | (200%, R.T.) % Force Relaxation @ 200% % |
| 2-5 | 130 | 1.40 | 74.4 | 1.80 | 38.9 |
| 2-6 | 112 | 2.37 | 83.5 | 2.80 | 41.4 |
| 2-7 | 112 | 2.76 | 78.4 | 3.37 | 35.1 |

[1]Modified hysteresis test (initial 300% cycle, followed by 2$^{nd}$ 200% cycle (hold for 30 sec at 200%))

As can be seen, blending PARAFILM M into VISTAMAXX results in large % set values in the film as a result of pre-straining; The higher the strain, the higher the set (>80% set for a blend containing 60% PARAFILM strained up to 300% at R.T.). It is believed that the PARAFILM M lowers the stress required to deform the material up to a given strain, whether during the initial cycle or at low strains in subsequent cycles. Said another way, it provides the plasto-elastic functionality with as soft touch and feel that nicely complement the conforming fit benefit from the VISTAMAXX. As can be seen, Adding a linear low density polyethylene component (with more or less crystallinity) to the blends tends to increase both loading and loading stresses, without much influence on the amount of set and/or force relaxation. The % force relaxation at body temperature after 10 hrs increases with the addition of PARAFILM, an indication of a partial loss in the elastic/recoverable characteristics of the material.

Table 7 illustrates the amount of permanent deformation (expressed in terms of specimen length relative to initial sample length) for the above material compositions when subjected to 2 successive deformation cycles up to 300% or 500% (of the original sample length in both deformations) at room temperature (~23° C.). Compression-molded film samples were used having 5 mm width and 2 cm length. The samples were hand-strained to a first stretch dimension (i.e. 300% for VM1, 500% for the plasto-elastic compositions 2-2-2-7), held for 3 sec and allowed to relax for 5 min before the operation was repeated.

TABLE 7

| Blend ID | Initial Dimension (cm; %) | First Stretch Dimension (cm; %) | First Relaxed Dimension (cm; %) | Second Stretch Dimension (cm; %) | Second Relaxed Dimension (cm; %) |
|---|---|---|---|---|---|
| 2-1 | 2; 100% | 6; 300% | 2.3; 115% | 6; 300% | 2.3; 115% |
| 2-2 | 2; 100% | 10; 500% | 3.1; 155% | 10; 500% | 3.15; 158% |
| 2-3 | 2; 100% | 10; 500% | 3.1; 155% | 10; 500% | 3.2; 160% |
| 2-4 | 2; 100% | 10; 500% | 3.0; 150% | 10; 500% | 3.15; 158% |
| 2-5 | 2; 100% | 10; 500% | 3.7; 185% | 10; 500% | 3.85; 193% |
| 2-6 | 2; 100% | 10; 500% | 4.5; 225% | 10; 500% | 4.65; 233% |
| 2-7 | 2; 100% | 10; 500% | 4.6; 230% | 10; 500% | 4.75; 238% |

As can be seen, the plasto-elastic blends (2-2 to 2-7) exhibit an increase in permanent size in the range of 50% to 125% as the result of the incorporation of various amounts of PARAFILM. The addition of LLDPE or VLDPE to PARAFILM further enhances the % set in blends when PARAFILM is the majority component of the blend. It should also be noted that set does not substantially increase on an additional strain cycle. For example, the difference in % set between the first and second cycle is typically less than 10% and often less than 5%. This is an indication of the excellent dimensional stability of the plasto-elastic composition beyond the prestraining cycle. Said another way, there is substantially elastic behavior after the first prestraining cycle.

Example 3

This example illustrates the effect on a variety of elastomeric materials due to the addition of a commercial soft, deformable polyolefin-based material (PARAFILM M).

The following materials were compounded in a batch mixer available from Haake Polylab of Newington, N.H. Fifty gram batches were processed for about 6 min at 170° C. Commercially available antioxidants were also added to the mix at a low level (<1%) to help protect the blend from thermal/oxidative degradation. Table 8 describes the compositions that were prepared (all values in wt. percent).

TABLE 8

| Blend ID | Polyolefin Material[1] | Styrenic Block Copolymer Blend[2] | Very Low Density Polyethylene[3] | Linear Low Density Polyethylene[4] | VLDPP[5] | Metallocene Polypropylene[6] |
|---|---|---|---|---|---|---|
| 3-1 | 40 | 60 | | | | |
| 3-2 | 60 | 40 | | | | |
| 3-3 | 40 | | 51 | 9 | | |
| 3-4 | 60 | | 34 | 6 | | |
| 3-5 | 40 | | | | 51 | 9 |
| 3-6 | 60 | | | | 34 | 6 |
| 3-7 | 50 | 30 | 17 | 3 | | |
| 3-8 | 50 | 30 | | | 17 | 3 |
| 3-9 | 50 | 25 | | | 21.25 | 3.75 |

[1] PARAFILM M is a polyolefin laboratory film commercialized by American National Can of Chicago, IL. The film was cut into pieces prior to being added to the batch mixer.
[2] A high-performance blend typically used in diaper stretch components. It consists of a Styrenic Block Copolymer available from Kuraray Co. Ltd. of Tokyo, Japan as Septon 4033, a polystyrene grade from Nova Chemicals of Pittsburgh, PA as PS3190 and an oil available from Penreco of The Woodlands, TX as Drakeol 600 that are blended together at a 55/10/35 ratio.
[3] EXACT 4049 (MI = 4.5 g/10 min; Density = 0.873 g/cm$^3$) available from Exxon Mobil Chemical Co of Huston, TX.
[4] LL6201 (MI = 50 g/10 min, Density = 0.926 g/cm$^3$), available from Exxon Mobil Chemical Co of Huston, TX.
[5] VLDPP MARS 3900 (MFR~3 g/10 min; density = 0.862 g/cm$^3$) is a very low density polypropylene material that is described in US Pat. 6,555,643.
[6] A metallocene polypropylene (MFR = 8 g/10 min; Density = 0.950 g/cm$^3$) as is available from Atofina Petrochemicals of Huston, TX as EOD-00-07.
Note that in the case of the very low crystallinity polyolefin materials, a small fraction (up to about 15% in the composition created above) of a higher crystallinity material may be added Compression-molded films were prepared with a Carver press using the method described in Example 2. Force relaxation (Table 9) and hysteresis testing (Table 10) was carried out according to the methods described above and the data are shown in the following tables (A minimum of two specimens was analyzed for each reported value):

As can be seen, adding PARAFILM M results in large % set values in the film during prestraining for a variety of elastomeric materials. At comparable PARAFILM/elastomer blend compositions, the styrene block copolymer-based blend exhibits the least amount of set as well as the lowest amount of force relaxation, whether the latter is measured at

TABLE 9

| Blend ID | Pre-strain Temperature (° C.) | Specimen Width (mm) | Film Basis weight (g/m$^2$) | Initial load @ 50% strain[1,2] (N) | Final load @ 50% strain[1,2] (N) | Force Relax. after 10 hrs (%) |
|---|---|---|---|---|---|---|
| 3-1 | 23 | 13 | 118 | 0.57 | 0.23 | 60 |
| 3-2 | 23 | 13 | 152 | 0.63 | 0.22 | 66 |
| 3-3 | 23 | ¼ | 118 | 2.68 | 1.08 | 60 |
| 3-4 | 23 | 13 | 144 | 2.19 | 0.80 | 63 |
| 3-5 | 23 | 13 | 133 | 0.99 | 0.31 | 68 |
| 3-6 | 23 | 25 | 108 | 0.84 | 0.25 | 70 |
| 3-7 | 23 | 13 | 140 | 1.23 | 0.51 | 59 |
| 3-8 | 23 | 13 | 130 | 0.74 | 0.30 | 60 |
| 3-9 | 23 | 13 | 124 | 0.78 | 0.23 | 71 |

[1] Normalized to 150 g/m$^2$ and 6.4 mm width
[2] Strained to 50% before reaching temperature equilibrium in environmental chamber

TABLE 10

| | | 1st Cycle (200%, RT) | | 2nd Cycle (50%, R.T.) | | | |
|---|---|---|---|---|---|---|---|
| Sample ID | Basis Weight g/m$^2$ | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 3-1 | 137 | 1.71 | 15 | 0.82 | 17.2 | 0.35 | 7.2 |
| 3-2 | 114 | 1.21 | 30 | 0.53 | 26.5 | 0.13 | 8.5 |
| 3-3 | 125 | 4.03 | 89 | 3.69 | 25.4 | 0.60 | 10.0 |
| 3-4 | 139 | 3.61 | 98 | 3.44 | 28.3 | 0.40 | 12.4 |
| 3-5 | 143 | 2.60 | 41 | 1.24 | 36.8 | 0.15 | 8.0 |
| 3-6 | 123 | 2.04 | 67 | 1.26 | 43.2 | 0.04 | 12.5 |
| 3-7 | 133 | 2.21 | 64 | 1.50 | 23.9 | 0.35 | 8.3 |
| 3-8 | 138 | 1.78 | 31 | 0.82 | 29.7 | 0.17 | 7.4 |
| 3-9 | 137 | 1.59 | 38.5 | 0.82 | 31.8 | 0.13 | 9.9 | room temperature after 30 sec or after 10 hrs at body temperature. Normalized load values also remain relatively low. The elastomeric polypropylene-based grades (compositions 2-2 and 2-5 of Example 2) exhibit higher set values, somewhat higher force relaxation as well as slightly higher load values. The elastomeric polyethylene blends exhibit the highest % set values (large shaping component), high load values and relatively low force. Also, tri-component blends that combine PARAFILM with two different types of elastomers (as illustrated by compositions 3-7 to 3-9) may be created to further tailor the balance of properties of the blend to those required for any specific application.

Example 4

This example illustrates the effect on tensile properties of a commercial elastomeric polypropylene grade (VISTAMAXX) by the addition of wax/polyolefin mixtures.

The following blends were compounded in a batch mixer available from Haake Polylab of Newington, N.H. Fifty gram batches were processed for about 6 min at 170° C. Commercially available antioxidants were also added to the mix at a low level (<1%) to help protect the blend from thermal/oxidative degradation. Compositions according Table 11 were prepared (values expressed in weight %).

TABLE 11

| | Blend Component | | | | | | | |
|---|---|---|---|---|---|---|---|---|
| | Elastomeric PP | | | | Low | | | Very Low |
| Blend ID | Polypropylene Random Copolymer[1] | Reactor Blend Polypropylene[2] | Linear Low Density Polyethylene[3] | Microcrystalline Wax[4] | Low Molecular Weight Polyethylene/Wax[5] | Molecular Weight Polyethylene[6] | Polypropylene Wax[7] | Molecular Weight Polyisobutylene[8] |
| 4-1 | 60 | | 8 | | 24 | | | 8 |
| 4-2 | 60 | | 8 | | 32 | | | |
| 4-3 | 60 | | 8 | 32 | | | | |
| 4-4 | 50 | 10 | 8 | | 32 | | | |
| 4-5 | 40 | | 12 | | 48 | | | |
| 4-6 | 60 | | | | 20 | 20 | | |
| 4-7 | 60 | | 10 | | 10 | | 20 | |

[1]Available from Exxon Mobil Chemical of Huston, TX as VISTAMAXX 1100.
[2]Soft polypropylene-based thermoplastic elastomer reactor blend produced using Catalloy technology and available as ADFLEX 7353 from Basell Polyolefins of Elkton, MD.
[3]Linear low density polyethylene (Melt Index = 50 g/10 min, Density = 0.926 g/cm$^3$) as is available as LL6201 from Exxon Mobil Chemical Co of Huston, TX.
[4]Microcrystalline wax available from the Crompton Corporation of Middlebury, CT as MULTIWAX W-835. Refined Wax 128 is a low melting refined petroleum wax available from the Chevron Texaco Global Lubricants of San Ramon, CA.
[5]A low molecular weight polyethylene as is available for Honeywell Specialty wax and additives of Morristown, NJ as A-C 735.
[6]A low molecular weight polypropylene as is available from Clariant, Pigments & Additives Division of Coventry, RI as LICOWAX PP230.
[7]A very low molecular weight polyisobutylene as is available from BASF of Ludwigshafen, Germany as OPPANOL B. Compression-molded films were prepared with a Carver press using the method described in Example 2. Force relaxation and hysteresis testing was carried out according to the methods described above and the data are shown in Tables 12 and 13 below (minimum of two specimens):

TABLE 12

| Blend ID | Prestrain Temperature (° C.) | Specimen Width (mm) | Film Basis Weight (g/m$^2$) | Initial load @ 50% Strain[1] (N) | Final load @ 50% Strain[1] (N) | Force Relaxation (%) |
|---|---|---|---|---|---|---|
| 4-1 | 23 | 25 | 115 | 0.39 | 0.11 | 72 |
| 4-2 | 23 | 25 | 107 | 0.46 | 0.16 | 66 |
| 4-3 | 23 | 25 | 118 | 0.43 | 0.13 | 70 |
| 4-4 | 23 | 25 | 122 | 0.65 | 0.28 | 57 |
| 4-5 | 23 | 25 | 86 | 0.64 | 0.24 | 62 |
| 4-6 | 23 | 13 | 137 | 0.79 | 0.31 | 60 |
| 4-7 | 23 | 13 | 126 | 0.95 | 0.45 | 53 |

[1]Normalized to 150 g/m$^2$ and 6.4 mm width

TABLE 13

| | | 1st Cycle (200%, RT) | | 2nd Cycle (50%, R.T.) | | |
|---|---|---|---|---|---|---|
| Blend ID | Basis Weight g/m$^2$ | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 4-1 | 124 | 1.56 | 29.3 | 0.78 | 30.0 | 0.15 | 10.0 |
| 4-2 | 115 | 1.62 | 39.3 | 0.94 | 30.6 | 0.15 | 9.8 |
| 4-3 | 132 | 1.11 | 28.4 | 0.64 | 29.0 | 0.14 | 9.0 |
| 4-4 | 131 | 2.07 | 39.3 | 1.10 | 32.3 | 0.16 | 10.8 |
| 4-5 | 90 | 1.92 | 94.9 | 1.63 | 45.8 | 0 | 20.5 |
| 4-6 | 131 | 1.86 | 20.4 | 1.02 | 21.9 | 0.39 | 7.0 |
| 4-7 | 127 | 2.59 | 24.5 | 1.16 | 27.5 | 0.35 | 6.9 |

As can be seen, various combinations of high molecular weight polyethylene, molecular weight polyethylene, polyethylene wax and polypropylene wax can be blended with a polypropylene-based elastomer to provide a blend with a combination of plastic and elastic properties. Adding a fraction of reactor blend elastomeric polypropylene not only lowers the amount of force relaxation but also increases stress values.

Example 5

This example describes film formation from blends of an isotactic polypropylene with stereoerrors along the polymer chain as disclosed in U.S. Pat. No. 6,555,643 the isotactic polypropylene resin was blended with various modifiers as described in Table 14. Samples 5-1 to 5-5 were compounded (including commonly used stabilizer materials such as antioxidants and the like at <1% of the blend) using a laboratory-scale mixer available from C. W. Brabender Instruments of Hackensack, N.J. The films were compression molded into films having a thickness of ~200μ by heating to ~200° C. and compressing between PTFE sheets in a Carver Press using a method similar to steps 1 through 14 in the Hysteresis Test method described below.

TABLE 14

| Sample | Polymer According to U.S. Pat. No. 6,555,643 (%) | Modifier (%) | Film Caliper (μ) |
|---|---|---|---|
| 5-1 | 100 | — | 162 |
| 5-2 | 85 | 15[a] | 218 |
| 5-3 | 70 | 30[a] | 229 |
| 5-4 | 55 | 45[a] | 198 |
| 5-5 | 70 | 30[b] | 201 |

[a]Experimental metallocene polypropylene having a melt flow rate of 8 grams/10 minutes from Ato-Fina Chemicals of Houston TX as code EOD 00-07
[b]Polypropylene-based nanoclay concentrate available from PolyOne of Arlington Heights, IL PolyOne 1001 master batch concentrate (50% clay).

The properties according to the Hysteresis Test for these blends are shown in Table 15.

TABLE 15

| | | 1st Cycle (200%, RT) | | | 2nd Cycle (50%, R.T.) | | |
|---|---|---|---|---|---|---|---|
| Blend ID | Basis Weight g/m² | Stress @ 200% Prestrain MPa | % Set after 1st Cycle % | Stress @ 50% MPa | % Force Relaxation @ 50% % | Stress @ 30% Unload MPa | % Set after 2nd Cycle % |
| 5-1[1] | 154 | 2.74 | 3.9 | 1.24 | 18.8 | 0.64 | 6.7 |
| 5-2 | 185 | 3.49 | 17.8 | 1.81 | 28.3 | 0.60 | 5.0 |
| 5-3 | 192 | 6.93 | 34.8 | 3.04 | 42.2 | 0.28 | 11.3 |
| 5-4 | 167 | 8.91 | 76.0 | 7.51 | 55.2 | 0.19 | 12.0 |
| 5-5 | 167 | 7.15 | 30.7 | 2.80 | 43.7 | 0.30 | 8.2 |

[1]Data same as Blend 1-3

Test Methods

Apparatus

Tensile Tester: A commercial constant rate of extension tensile tester from Instron Engineering Corp., Canton, Mass. or SINTECH-MTS Systems Corporation, Eden Prairie, Minn. (or a comparable tensile tester) may is suitable. The instrument is interfaced with a computer for controlling the test speed and other test parameters, and for collecting, calculating and reporting the data.

Load Cell Choose the jaws and load cell suitable for the test; the jaws should be wide enough to fit the sample, typically 2.54 cm jaws are used; the load cell is chosen so that the expected tensile response from the sample tested will be between 25% and 75% of the capacity of the load cells or the load range used, typically a 1 kN load cell is used;

Sample Cutter The specific sample cutter is defined by the desired sample width. Suitable cutters are available from Thwing-Albert Instrument Co. of Philadelphia, Pa. For a 2.54 cm wide sample a Model JDC 1-10 is suitable.

Sample Preparation

The plasto-elastic material is first separated from any substrate or other material to which it is attached by any suitable means. One such means is to freeze the sample so as to reduce the bond strength between the plasto-elastic material and other materials. A suitable freezing medium is compressed 1,1,1,2 tetrafluoroethane sold under the trade name QUICK-FREEZE by Miller-Stephenson Chemical Company of Danbury, Conn.

Separate enough sample to prepare at least three specimens 2.5 cm×5 cm (~15 grams). The Specimens are prepared using the following method:

1) Weigh approximately 12 grams of the elastomeric composition of interest.
2) Compression mold the composition by placing the pre-weighed material between two pieces of 0.010 inch (0.03 mm) caliper PTFE (Teflon®) film.
3) Place the film "sandwich" between preheated aluminum plates that are inserted into a Carver Press model 3853-0 with heated plates set to approximately 200° C.
4) Heat the material for 3 minutes and then pressing it between the plates with an applied pressure of 17 MPa.
5) Allow the formulation to flow under pressure for 30 seconds.
6) Quench the resulting film to ambient temperature.
7) Cut the sample into three equal portions.
8) Place each portion between films of PTFE and preheated aluminum plates and allowed to heat up to 160° C. for 1 minute in the Carver press before 14 MPa of pressure is applied.
9) Allow the sample to flow under pressure for 30 seconds.
10) Release the pressure is removed and rotate the sample 90°. Insert the sample back into the press and immediately apply a pressure of 21 MPa.
11) The sample is again allowed to flow for 30 seconds. The pressure is released and the sample is flipped, inserted back into the press and immediately 28 MPa of pressure is applied.
12) The sampled is again allowed to flow for 30 seconds.
13) The pressure is removed and the sample is rotated 90° and inserted back into the press and immediately 34 MPa psi of pressure is applied.
14) The sample is again allowed to flow for 30 seconds.

15) After the final pressing, the sample is allowed to cool to ambient temperature. The resulting film thickness is between 4 mils up to 15 mils thick
16) Cut the resulting sample into a 2.5 cm×5 cm rectangle. All testing is done at ambient laboratory conditions (~25° C., 50% RH).

First Strain (Shaping Strain) Hysteresis Cycle:
1) Samples are placed in the tensile tester jaws with a 2.5 cm gauge length. Otherwise, mount the sample between the jaws of the tensile tester using the maximum gap allowed by the sample length.
2) Strain the sample to a maximum strain of 200% (i.e., the sample is 3× its initial length) at a strain rate of 25.4 cm/min. Particular samples may be strained to other maximum strains in specific instances. If a maximum strain other than 200% is used, that strain should be recorded and used in the % Set calculation.
3) At 200% strain (7.5 cm jaw separation) the direction of jaw displacement is reversed and the jaw returns to its original position at a rate of 25.4 cm./min.
4) Allow the sample to relax at zero strain for one minute.
5) After one minute, the samples are reloaded at a strain rate of 25.4 cm./min up to a load of 0.10 N to pull out slack in the sample. Measure and record the separation between the jaws.
6) Calculate % set according to the following equation (The % set determines the extent of permanent plastic deformation built into the material as a result of the prestraining process.):

$$\% \text{ Set} = \left[ \frac{\text{Jaw Gap after Step 5} - \text{Gage Length}}{\text{GageLength}} \right] \times 100$$

7) A minimum of 3 samples is tested and the data averaged.
8) Report the following:
   i) Maximum load at 200% strain (or other value of maximum strain) in N/cm.
   ii) % set (As will be recognized, the difference (100−% set) in turn provides the % extent of recoverable elastic deformation intrinsic to the material.)

Second Strain Hysteresis Cycle:
1) Clamp a sample prestrained according to the First Hysteresis Loading Cycle between a pair of jaws with set to a gage length of 2.5 cm pulling gently to remove any slack.
2) After 2 minutes, extend the sample to 50% strain (1.5× initial length) at a rate of 25 cm/min.
3) Hold the sample at 50% strain for a period of 30 seconds and the force is monitored (e.g., collected by the associated computer) as a function of time over that period.
4) Return to the original length at 10 in./min and hold for 60 seconds.
5) After one minute, the samples are reloaded at a strain rate of 25.4 cm./min up to a load of 0.10 N to pull out slack in the sample. Measure and record the separation between the jaws.
6) Measure the % set upon reloading following the same protocol described in the method outlined above.

$$\% \text{ Set} = \left[ \frac{\text{Jaw Gap after Step 5} - \text{Gage Length}}{\text{Gage Length}} \right] \times 100$$

7) A minimum of 3 samples is tested and the data averaged.
8) Report the following for each of three samples:
   a. The load at 50% strain (N/cm)
   b. % set
   c. % force relaxation at 50% during the 30 second hold time in the second hysteresis cycle; It is determined using the following formula:

$$\% \text{ Force relaxation} = \frac{\left[ \begin{array}{l} (\text{Load at 50\% before hold time}) - \\ (\text{Load at 50\% after hold time}) \end{array} \right]}{(\text{Load at 50\% before hold time})}$$

Force Relaxation at Body Temperature (38° C.):
1) Clamp a sample prestrained according to the First Hysteresis Loading Cycle between a pair of jaws with set to a gage length of 2.5 cm pulling gently to remove any slack. For this test the jaws and sample are in an environmental chamber maintained at 38° C. and the sample is allowed to equilibrate in the chamber (~1 minute) before it is extended.
2) Extend the sample to 50% strain (1.5×initial length) at a rate of 25 cm/min.
3) Hold the sample at 50% strain for a period of 10 hours
4) Monitor and record the initial force after the extension step and the force at 1, 4 and 10 hrs at 38° C.
5) Calculate and report % force relaxation for three samples at each time period, using the following equation:

$$\frac{\% \text{ Force relaxation}}{(\text{at 38 C \& at time } t)} = \frac{\left[ \begin{array}{l} (\text{Initial load at 50\%}) - \\ (\text{Load at time } t) \end{array} \right]}{(\text{Initial load at 50\%})}$$

Dimensional Stability in Storage Conditions
This method is based on ASTM standard method D 1204-02:
1) Prestrain a sample according to the First Hysteresis Loading Cycle
2) Carefully measure the length and width dimensions of the sample and a permanent marker is used to trace equidistant points at 10 or 5 mm intervals (depending upon the initial size of the specimens) in both dimensions.
3) Place the sample on a sand bed (replaces paper and talc of the ASTM method) and into a controlled thermal chamber at a temperature of 60° C.
4) Remove the sample after two minutes.
5) Measure both dimensions after the exposure to 60° C.
6) Calculate the change in both dimensions as a percentage of the original dimension. A value above 100% is indicative of an expansion of the material in that particular direction as a result of exposure to heat (annealing). A value lower than 100% is indicative of a contraction of the specimen.
7) Report the results for three samples.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a plasto-elastic material wherein said plasto-elastic material comprises a combination of an elastomeric polypropylene and a second polyolefin, said combination being selected from polymeric blends or polymeric mixtures, such that:
   a) said material has substantially plastic properties when said absorbent article is subjected to an initial strain cycle such that said material is provided with a set of at least 30% by said initial strain cycle; and
   b) said material has substantially elastic properties when subjected to at least a second strain cycle, said substantially elastic properties serving to facilitate conformity of said article to a wearer's body shape; and
      wherein said absorbent article has a waist region, a crotch region, a longitudinal centerline and a lateral centerline and said absorbent article additionally comprises at least one feature selected from the group consisting of a liquid permeable topsheet, a liquid impermeable backsheet, an absorbent core disposed between said topsheet and said backsheet, a side panel, a waist band, a belt, a fastener component and combinations thereof; wherein said plasto-elastic material is joined to or disposed on at least one of said features in a stretch zone.

2. An absorbent article according to claim 1 wherein said feature having a plasto-elastic material joined thereto or disposed thereon is selected from the group consisting of a side panel, waist feature and a belt.

3. An absorbent article according to claim 1 wherein said plasto-elastic material is disposed on said feature in a linear stretch zone.

4. An absorbent article according to claim 3 wherein said linear stretch zone is disposed at an angle of between about −70° and about +70° with respect to said lateral centerline.

5. An absorbent article according to claim 4 wherein said linear stretch zone is disposed at an angle between 0° and about +50° with respect to said lateral centerline.

6. An absorbent article according to claim 4 wherein said absorbent article comprises at least two linear stretch zones, said linear stretch zones being disposed at different angles with respect to said lateral centerline.

7. An absorbent article according to claim 6 wherein said absorbent article comprises a first linear stretch zone disposed at an angle between 0° and about +50° with respect to said lateral centerline and a second linear stretch zone disposed at an angle between 0° and about +50° with respect to said lateral centerline.

8. An absorbent article according to claim 1 wherein said stretch zone is a curvilinear stretch zone, at least a portion of said curvilinear stretch zone having a radius of curvature between about 1 mm and about 1 m.

9. An absorbent article according to claim 1 wherein said stretch zone has a width dimension of at least about 0.2 mm.

10. An absorbent article according to claim 1 wherein said stretch zone has a thickness dimension of at least about 0.1 mm.

11. An absorbent article according to claim 1 wherein said stretch zones are disposed in an array selected from the group consisting of continuous arrays and intermittent arrays.

12. An absorbent article according to claim 11 wherein said array comprises a plurality of stretch zones having a spacing therebetween and said spacing is selected from the group consisting of uniform spacing and non-uniform spacing.

13. An absorbent article according to claim 11 wherein said absorbent article comprises first and second arrays of individual stretch zones and said first and second arrays differ in spacing between said stretch zones having a first spacing and a second spacing said first spacing is between about 0.5-mm and about 5 mm and said second spacing is between about 2 mm and about 20 mm.

14. An absorbent article according to claim 11 wherein said array comprises at least two differing individual stretch zones.

15. An absorbent article according to claim 1 wherein said feature comprises a plasto-elastic material disposed on a substrate wherein said substrate limits the maximum elongation of the material during said initial strain cycle such that said initial strain cycle elongates said plasto-elastic material no more than about 50%.

16. An absorbent article according to claim 1 wherein said absorbent article is a disposable diaper said disposable diaper being selected from the group consisting of pant style diapers and open style diapers.

* * * * *

UNITED STATES PATENT AND TRADEMARK OFFICE
CERTIFICATE OF CORRECTION

PATENT NO. : 8,182,456 B2
APPLICATION NO. : 11/087368
DATED : May 22, 2012
INVENTOR(S) : Jean-Philippe Marie Autran et al.

It is certified that error appears in the above-identified patent and that said Letters Patent is hereby corrected as shown below:

Column 36, Line 5 – delete "+50°" and insert -- -50° --

Signed and Sealed this
Thirty-first Day of July, 2012

David J. Kappos
*Director of the United States Patent and Trademark Office*